US010700308B2

United States Patent
Jin et al.

(10) Patent No.: US 10,700,308 B2
(45) Date of Patent: *Jun. 30, 2020

(54) AROMATIC AMINE COMPOUND, LIGHT-EMITTING ELEMENT MATERIALS AND LIGHT-EMITTING ELEMENT

(71) Applicant: TORAY INDUSTRIES, INC., Tokyo (JP)

(72) Inventors: Guangnan Jin, Shanghai (CN); Peng Wang, Shanghai (CN); Fangrong Xu, Shanghai (CN); Lingzhi Zhong, Shanghai (CN); Takeshi Ishigaki, Shanghai (CN); Daisaku Tanaka, Otsu (JP); Takeshi Ikeda, Otsu (JP); Takuya Nishiyama, Otsu (JP)

(73) Assignee: Toray Industries, Inc., Tokyo (JP)

( * ) Notice: Subject to any disclaimer, the term of this patent is extended or adjusted under 35 U.S.C. 154(b) by 175 days.

This patent is subject to a terminal disclaimer.

(21) Appl. No.: 15/108,126

(22) PCT Filed: Dec. 18, 2014

(86) PCT No.: PCT/CN2014/094227
§ 371 (c)(1),
(2) Date: Jun. 24, 2016

(87) PCT Pub. No.: WO2015/096658
PCT Pub. Date: Jul. 2, 2015

(65) Prior Publication Data
US 2016/0322606 A1 Nov. 3, 2016

(30) Foreign Application Priority Data
Dec. 26, 2013 (CN) .......................... 2013 1 0729370

(51) Int. Cl.
*H01L 51/50* (2006.01)
*C07D 401/14* (2006.01)
(Continued)

(52) U.S. Cl.
CPC ........ *H01L 51/5262* (2013.01); *C07D 401/14* (2013.01); *C07D 409/14* (2013.01); *C07D 495/14* (2013.01); *C09K 11/06* (2013.01); *H01L 51/006* (2013.01); *H01L 51/0052* (2013.01); *H01L 51/0061* (2013.01); *H01L 51/0067* (2013.01); *H01L 51/0068* (2013.01); *H01L 51/0072* (2013.01); *C09K 2211/1011* (2013.01); *C09K 2211/1014* (2013.01);
(Continued)

(58) Field of Classification Search
CPC ............ H01L 51/5262; H01L 51/0052; H01L 51/006; H01L 51/0061; H01L 51/0067; H01L 51/0068; H01L 51/0072; H01L 51/0058; H01L 51/5012; C07D 401/14; C07D 409/14; C07D 495/14; C09K 11/06; C09K 221/1011; C09K 221/1014; C09K 221/1029; C09K 221/1044; C09K 221/1088; C09K 221/1092
See application file for complete search history.

(56) References Cited

U.S. PATENT DOCUMENTS

2005/0116626 A1* 6/2005 Cheng ................. C07F 15/0033
313/504
2012/0138918 A1 6/2012 Naraoka et al.
(Continued)

FOREIGN PATENT DOCUMENTS

CN 101944570 A 1/2011
JP 2006063043 A 3/2006
(Continued)

OTHER PUBLICATIONS

JP2006063043A, Tanabe et al., English machine translation (Year: 2006).*
(Continued)

*Primary Examiner* — Susan D Leong
(74) *Attorney, Agent, or Firm* — RatnerPrestia

(57) ABSTRACT

Provided are an aromatic amine compound as represented by formula (1), $$\begin{array}{c} Ar^1 \diagdown_N \diagup L^1 \diagdown_X \diagup L^2 \diagdown_N \diagup Ar^2 \\ Ar^3 \diagup \qquad \diagdown_{R^1} \diagdown_{R^2} \diagup \qquad \diagdown Ar^4 \end{array} \qquad (1)$$

used for improving light extraction efficiency and color purity of an organic light-emitting element, an organic light-emitting element material containing the aromatic amine compound, an organic light-emitting element covering layer material containing the aromatic amine compound, and an organic light-emitting element containing the aromatic amine compound. The organic light-emitting element achieves high light-emitting efficiency and color reproducibility. The organic light-emitting element can be used as organic EL display, backlight source for liquid crystal display, illumination, light source for measurement devices, indication board or identification lamp etc. The organic light-emitting element significantly improves light extraction efficiency and has superior color purity.

5 Claims, No Drawings

(51) Int. Cl.
*C07D 409/14* (2006.01)
*C07D 495/14* (2006.01)
*C09K 11/06* (2006.01)
*H01L 51/52* (2006.01)
*H01L 51/00* (2006.01)

(52) U.S. Cl.
CPC ............ *C09K 2211/1029* (2013.01); *C09K 2211/1044* (2013.01); *C09K 2211/1088* (2013.01); *C09K 2211/1092* (2013.01); *H01L 51/0058* (2013.01); *H01L 51/5012* (2013.01)

(56) References Cited

U.S. PATENT DOCUMENTS

| | | | | |
|---|---|---|---|---|
| 2012/0217492 | A1* | 8/2012 | Kim | C07D 209/80 257/40 |
| 2017/0018733 | A1* | 1/2017 | Jin | H01L 51/5275 |

FOREIGN PATENT DOCUMENTS

| | | | |
|---|---|---|---|
| JP | 2006156390 | | 6/2006 |
| JP | 2006302878 | | 11/2006 |
| JP | 2007103303 | | 4/2007 |
| JP | 2008133225 | | 6/2008 |
| JP | 2008166558 A | * | 7/2008 |
| WO | 2011043083 | | 4/2011 |
| WO | 2001039554 | | 5/2016 |

OTHER PUBLICATIONS

JP-2008166558-A, Iwamoto, Shintaro English machine translation (Year: 2008).*
Extended European Search Report for European Application No. 14875253.8, dated May 11, 2017, 6 pages.
Li et al., "Temperature effect on liquid crystal refractive indices", Journal of Applied Physics, vol. 96, No. 19, 2004 (Abstract Only).
Madigan et al., "Improvement of output coupling efficiency of organic light-emitting diodes by backside substrate modification", Journal of Applied Physics Letters, vol. 76, No. 1650, 2000 (Abstract Only).
International Search Report and Written Opinion of the International Search Authority for International Application No. PCT/CN2014/094227, dated Mar. 23, 2015.
English translation of Chinese Office Action for Application No. 201480070874.2, dated Mar. 24, 2017, 8 pages.
European Communication for European Application No. 14 875 253.8, dated Jan. 2, 2019—4 pages.

* cited by examiner

AROMATIC AMINE COMPOUND, LIGHT-EMITTING ELEMENT MATERIALS AND LIGHT-EMITTING ELEMENT

CROSS REFERENCE TO RELATED APPLICATIONS

This is the U.S. National Phase application of PCT International Application No. PCT/CN2014/094227, filed Dec. 18, 2014, and claims priority to Chinese Patent Application No. 201310729370.4, filed Dec. 26, 2013, the disclosures of each of these applications being incorporated herein by reference in their entireties for all purposes.

FIELD OF THE INVENTION

The present invention relates to aromatic amine compound for organic light-emitting element, light-emitting element material and light-emitting element containing the aromatic amine compound, and more particularly relates to aromatic amine compound for organic light-emitting element, light-emitting element material, light-emitting element that has significantly improved light extraction efficiency.

BACKGROUND OF THE INVENTION

An organic light-emitting element represents a self-emissive display device, having advantages relating to thinness, light weight, wide view angle, low power consumption, high contrast, etc.

The light-emitting principle of organic light-emitting element is that holes and electrons are introduced by electrode injection, the light is generated when holes and electrons recombine in light-emitting layer and return to the ground state from the excited state. As such light-emitting elements have characteristics of being advantageously thin and being capable of emitting high brightness light at low driving voltage and emitting light in multiple colors by using different light-emitting materials, therefore, these light-emitting elements receive much concern.

Since C. W. Tang from Kodak Company reported that organic thin-film elements could emit light with high brightness, many researches have been made to applications of the organic thin-film elements. Organic thin-film light-emitting elements are now used in main screens of mobile phones and other devices, and significant progress is demonstrated on practicalization. However, there are various technical issues needs to be addressed. Particularly, realizing high efficiency and low power consumption of the element is one subject to be figured out.

Depending on the direction of the light from the organic light-emitting layer, the organic light-emitting elements are classified into two types, namely bottom-emitting organic light-emitting elements and top-emitting organic light-emitting elements. In a bottom-emitting organic light-emitting element, light is pointed to the substrate side. A reflective electrode is provided on the organic light-emitting layer, while a transparent electrode is provided at the lower section of the organic light-emitting layer. In this case, when the organic light-emitting element has an active matrix element, since the part where the thin-film transistor is formed is opaque, the light-emitting area is reduced. On the other hand, in a top-emitting organic element, the transparent electrode is formed at the upper section of the organic light-emitting layer, and the reflective electrode is formed at the lower section of the organic light-emitting layer, so the light is emitting in a direction opposite to the substrate side. Thus, the light-transmitting area is increased and the brightness is increased.

In the current technology, for improving light-emitting efficiency of the top-emitting organic light-emitting elements, one approach is to form an organic covering layer on the upper translucent metal electrode where the light form the light-emitting layer passes through, so as to modulate the optical interference distance, and control reflection of external light and extinction caused by energy movement of surface plasma (as described in Patent Documents 1 to 5).

For example, as described in Patent Document 2, an organic covering layer is formed on the upper translucent metallic electrode of the top-emitting organic light-emitting element and has a refractive index of 1.7 or more and a thickness of 600 Å, contributing to improving the light-emitting efficiency of the red and green organic light-emitting element to 1.5 times. The material of the organic covering layer uses an amine derivative or a quinolinol clathrate.

As described in Patent Document 4, materials whose energy gap is smaller than 3.2 eV have impact on the wavelength of blue light, and are not suitable for organic covering layers. The materials of the organic covering layer are amine derivatives having specific chemical structures.

Patent Document 5 describes that for the blue light-emitting element with low CIEy, the organic covering layer is made of a material having a variation of refractive index $\Delta n > 0.08$ in the wavelength range of 430 nm to 460 nm. The materials used for the organic covering layer are anthracene derivatives having specific chemical structures, etc.

Patent Documents Referred:
Patent Document 1: WO2001/039554;
Patent Document 2: JP2006-156390;
Patent Document 3: JP2007-103303;
Patent Document 4: JP2006-302878; and
Patent Document 5: WO2011/043083.
Non-Patent Document
Journal of Applied Physics, 96, 19 (2004).
Journal of Applied Physics Letters, 76, 1650 (2000).

BRIEF SUMMARY OF THE INVENTION

As described above, in the current technology, amine derivatives having specific structure of high refractive indexes or materials meeting certain parametric requirements are used as materials of the organic covering layer to improve light extraction efficiency and color purity. Nevertheless, the problem both covering the light-emitting efficiency and color purity is still not solved, especially in the cases of preparing the blue light-emitting elements.

The present invention provides an aromatic amine compound used for improving light extraction efficiency and color purity of an organic light-emitting element, an organic light-emitting element material containing the aromatic amine compound, an organic light-emitting element covering layer material containing the aromatic amine compound and an organic light-emitting component containing the aromatic amine compound.

The disclosed aromatic amine compound has a thiophene-based structure, a furan-based structure or a pyrrole-based structure, so the aromatic amine compound possesses superior thin-film stability and high refractive index, thereby improving both light extraction efficiency and color purity.

In the present invention, the aromatic amine compound is represented by Formula (1):

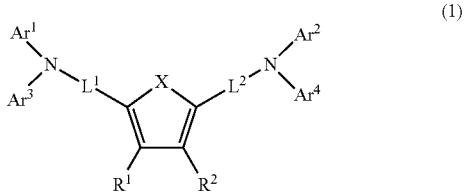

(1)

where X is a sulfur atom, an oxygen atom or N—R;

R is one or more selected from hydrogen, deuterium, substitutable alkyl, cycloalkyl, heterocyclyl, alkenyl, cycloalkenyl, alkynyl, alkoxy, alkylthio, arylether, arylsulfide, aryl, heteroaryl, carbonyl, carboxyl, oxycarbonyl, carbamoyl, alkylamino and silyl;

$L^1$, $L^2$ may be identical or different, and each is selected from arylene and heteroarylene;

$Ar^1$, $Ar^2$ may be identical or different, and each is selected from aryl and heteroaryl;

$Ar^3$, $Ar^4$ may be identical or different heteroaryl groups; and $R^1$~$R^2$ may be identical or different, and each is one or more selected from hydrogen, deuterium, halogen, substitutable alkyl, cycloalkyl, heterocyclyl, alkenyl, cycloalkenyl, alkynyl, alkoxy, alkylthio, arylether, arylsulfide, aryl, heteroaryl, cyano, carbonyl, carboxyl, oxycarbonyl, carbamoyl, alkylamino and silyl, and may be bonded with an adjacent substituent to form a ring.

From the aspect of easy synthesis and low cost, $L^1$ and $L^2$ are preferably arylene.

The present invention also provides an organic light-emitting element material, which contains the compound represented by Formula (1):

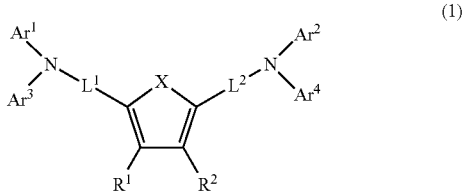

(1)

where X is a sulfur atom, an oxygen atom or N—R;

R is one or more selected from hydrogen, deuterium, substitutable alkyl, cycloalkyl, heterocyclyl, alkenyl, cycloalkenyl, alkynyl, alkoxy, alkylthio, arylether, arylsulfide, aryl, heteroaryl, carbonyl, carboxyl, oxycarbonyl, carbamoyl, alkylamino and silyl;

$L^1$, $L^2$ may be identical or different, and each is selected from arylene and heteroarylene;

$Ar^1$, $Ar^2$ may be identical or different, and each is selected from aryl and heteroaryl;

$Ar^3$, $Ar^4$ may be identical or different heteroaryl groups; and $R^1$~$R^2$ may be identical or different, and each is one or more selected from hydrogen, deuterium, halogen, substitutable alkyl, cycloalkyl, heterocyclyl, alkenyl, cycloalkenyl, alkynyl, alkoxy, alkylthio, arylether, arylsulfide, aryl, heteroaryl, cyano, carbonyl, carboxyl, oxycarbonyl, carbamoyl, alkylamino and silyl, and may be bonded with an adjacent substituent to form a ring. From the aspect of easy synthesis and low cost, $L^1$ and $L^2$ are preferably arylene.

The present invention provides an organic light-emitting element, which comprises a substrate, a first electrode, one layer or more of organic film including a light-emitting layer, and a second electrode element. The light-emitting element further comprises a covering layer. The covering layer contains an organic material, and the organic light-emitting element contains the foregoing organic light-emitting element material.

The present invention further provides an organic light-emitting element covering layer material, which contains the compound represented by Formula (1):

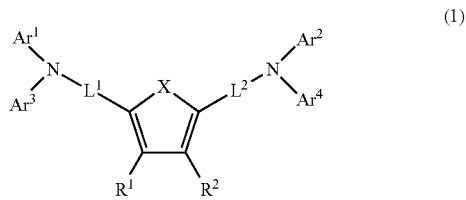

(1)

where X is a sulfur atom, an oxygen atom or N—R;

R is one or more selected from hydrogen, deuterium, substitutable alkyl, cycloalkyl, heterocyclyl, alkenyl, cycloalkenyl, alkynyl, alkoxy, alkylthio, arylether, arylsulfide, aryl, heteroaryl, carbonyl, carboxyl, oxycarbonyl, carbamoyl, alkylamino and silyl;

$L^1$, $L^2$ may be identical or different, and each is selected from arylene and heteroarylene;

$Ar^1$, $Ar^2$ may be identical or different, and each is selected from aryl and heteroaryl;

$Ar^3$, $Ar^4$ may be identical or different heteroaryl groups; and $R^1$~$R^2$ may be identical or different, and each is one or more selected from hydrogen, deuterium, halogen, substitutable alkyl, cycloalkyl, heterocyclyl, alkenyl, cycloalkenyl, alkynyl, alkoxy, alkylthio, arylether, arylsulfide, aryl, heteroaryl, cyano, carbonyl, carboxyl, oxycarbonyl, carbamoyl, alkylamino and silyl, and may be bonded with an adjacent substituent to form a ring.

From the aspect of easy synthesis and low cost, $L^1$ and $L^2$ are preferably arylene.

The present invention finally provides an organic light-emitting element, which comprises a substrate, a first electrode, one layer or more of organic film including a light-emitting layer, and a second electrode element. The light-emitting element further comprises a covering layer, and the organic light-emitting element contains the foregoing organic light-emitting element material. The disclosed aromatic amine compound has a thiophene-based structure, a furan-based structure or a pyrrole-based structure, so it possesses superior thin-film stability and high refractive index, therefore the problem of improving both the light extraction efficiency and the color purity can be solved.

DETAILED DESCRIPTION OF THE INVENTION

The covering layer material represented by Formula (1) has a thiophene-based structure, a furan-based structure or a pyrrole-based structure, so it possesses high glass transition temperature and steric hindrance effects, thereby showing superior thin-film stability. In addition, a thiophene-based structure, a furan-based structure or a pyrrole-based structure helps to improve a light-absorption coefficient and thereby contributes to a higher attenuation coefficient. This allows the thin film to have a higher refractive index in ultraviolet-visible range. Moreover, a heteroaryl group helps to improve polarizability, and further improves a refractive index. Moreover, when $Ar^1 \sim Ar^2$ are both aryl, although high refractive index is achieved, redshift of isosbestic wavelength may lead to absorption of the blue light and cause light-emitting efficiency lower. Thus, it is preferable that $Ar^3$ and $Ar^4$ are heteroaryl. Preferably, $Ar^3$ and $Ar^4$ have electron-withdrawing nitrogen atoms. That is, a nitrogen atom in a heteroaryl group connects to the adjacent atom with a double bond. This can not only suppress redshift of wavelength but also improve a refractive index. Preferably, $Ar^3$ and $Ar^4$ are pyridyl, quinolyl, pyrimidinyl or quinazolinyl quinoxalinyl. Furthermore they are preferably pyridyl, quinolyl or pyrimidinyl.

It is clear that when the covering layer is made of the aromatic amine compound having a high refractive index, the organic light-emitting element with a significantly improved light extraction efficiency and a superior color purity may be obtained.

The alkyl is preferably C 1-C20 alkyl; and more preferably one or more saturated aliphatic hydrocarbyls such as methyl, ethyl, n-propyl, isopropyl, n-butyl, sec-butyl and tert-butyl. The alkyl may be with or without a substituent.

The cycloalkyl is preferably C3-C20 cycloalkyl; and more preferably one or more saturated aliphatic cyclic hydrocarbyls such as cyclopropyl, cyclohexyl, norbornyl and adamantyl. The cycloalkyl may be with or without a substituent.

The heterocyclyl is preferably C2-C20 heterocyclyl; and more preferably one or more aliphatic rings having atoms other than carbon such as pyran ring, piperidine ring, and cyclic amide. The heterocyclyl may be with or without a substituent.

The alkenyl is preferably C2-C20 alkenyl; and more preferably one or more unsaturated aliphatic hydrocarbyls containing a double bond such as vinyl, allyl and butadienyl. The alkenyl may be with or without a substituent.

The cycloalkenyl is preferably C3-C20 cycloalkenyl; and more preferably one or more unsaturated aliphatic cyclic hydrocarbyls containing a double bond such as cyclopentenyl, cyclopentadienyl and cyclohexenyl. The cycloalkenyl may be with or without a substituent.

The alkynyl is preferably C2-C20 alkynyl; and more preferably an unsaturated aliphatic hydrocarbyl containing a triple bond such as ethynyl. The alkynyl may be with or without a substituent.

The alkoxy is preferably C1-C20 alkoxy; and more preferably one or more functional groups bonded with aliphatic hydrocarbyls via ether bonds such as methoxy, ethoxy and propoxy. The aliphatic hydrocarbyl may be with or without a substituent.

The alkylthio is a radical group in which oxygen atoms of alkoxy are replaced with sulfur atoms. It is preferably C1-C20 alkylthio; the alkyl of alkylthio may be with or without a substituent.

The aryl is preferably C6-C60 aryl; and more preferably one or more aromatic hydrocarbon groups such as phenyl, naphthyl, biphenyl, phenanthryl, terphenyl and pyrenyl. The aryl may be with or without a substituent.

The heteroaryl is preferably C4-C60 aromatic heterocyclyl; and more preferably one or more from furyl, thienyl, pyrrolyl, benzofuranyl, benzothienyl, dibenzofuranyl, dibenzothienyl, pyridyl and quinolyl. The aromatic heterocyclyl may be with or without a substituent.

The arylether is preferably C6-C40 arylether; and more preferably a functional group bonded with aromatic hydrocarbon groups via ether bonds such as phenoxy. The arylether may be with or without a substituent.

The arylsulfide is a radical group in which oxygen atoms of ether bonds of arylether are replaced with sulfur atoms. It is preferably C6-C60 arylsulfide. The aromatic hydrocarbon groups in arylsulfide may be with or without a substituent.

The halogen atom is selected from fluorine, chlorine, bromine and iodine.

The carbonyl, carboxyl, oxycarbonyl, carbamoyl, and alkylamino may be with or without a substituent. The number of carbon atoms in the alkylamino substituent is not limited, while it is usually in the range of 2 to 60.

The silyl is expressed as a functional group having bonds bonded to silicon atoms, such as trimethylsilyl, triethylsilyl, dimethyl tert-butyl silyl and triphenylsilyl. Silyl may be with or without a substituent. The number of carbon atoms in silyl is not limited, while it is usually in the range of 1 to 40.

The substituent is one or more selected from deuterium, halogen, C1-C15 alkyl, C3-C15 cycloalkyl, C3-C15 heterocyclyl, C2-C15 alkenyl, C4-C15 cycloalkenyl, C2-C15 alkynyl, C1-C55 alkoxy, C1-C55 alkylthio, C6-C55 arylether, C6-C55 arylsulfide, C6-C55 aryl, C4-C55 aromatic heterocyclyl, carbonyl, carboxyl, oxycarbonyl, carbamoyl, C1-C55 alkylamino, and C3-C15 silyl that has 1 to 5 silicon atoms.

While the aromatic amine compound is not particularly limited herein, the following are some preferred examples:

[1]

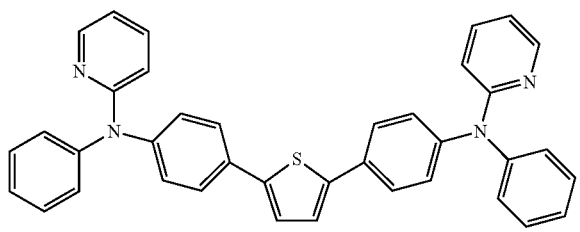

[2]

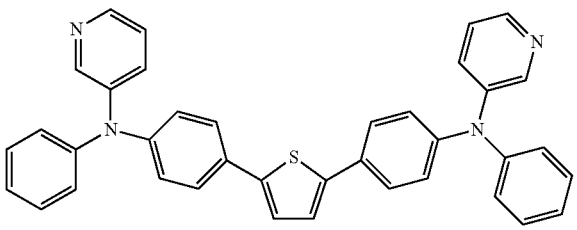

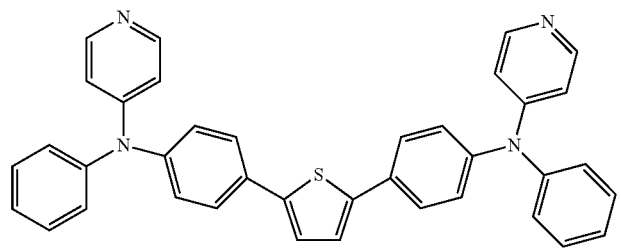
[3]
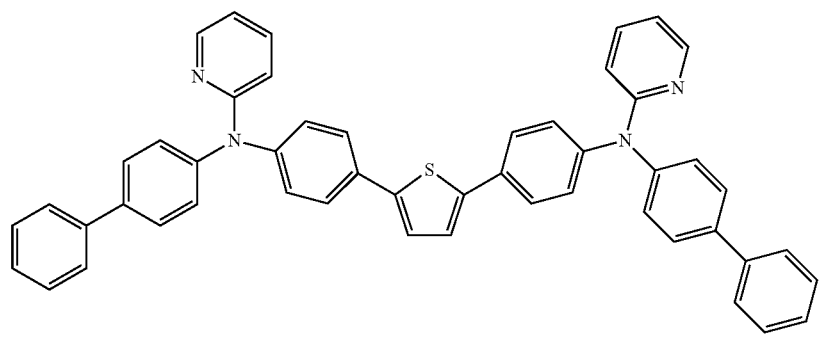
[4]
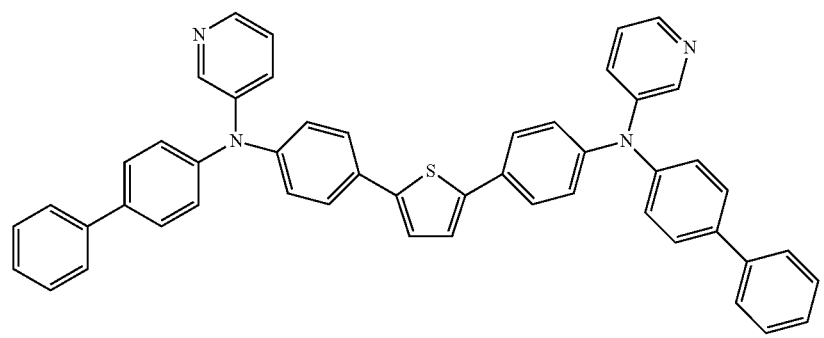
[5]
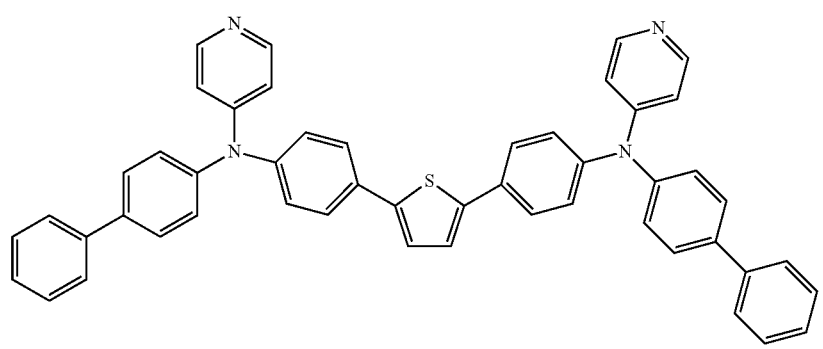
[6]
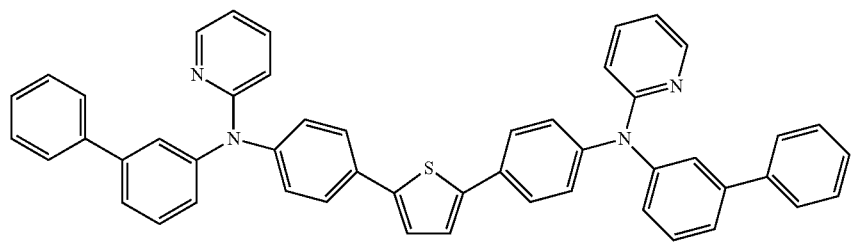
[7]

-continued
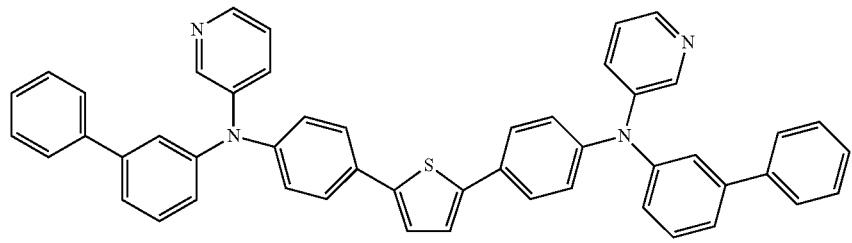
[8]
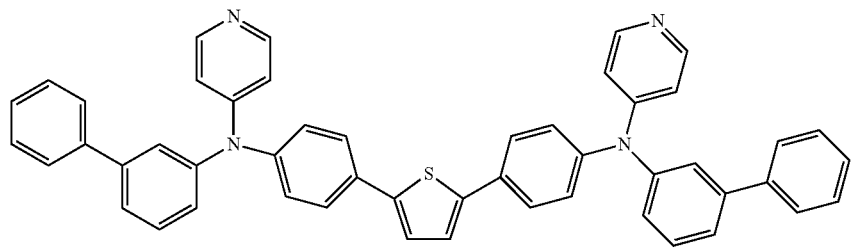
[9]
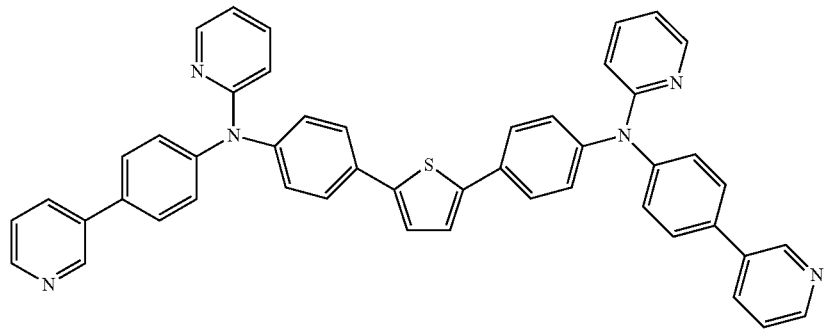
[10]
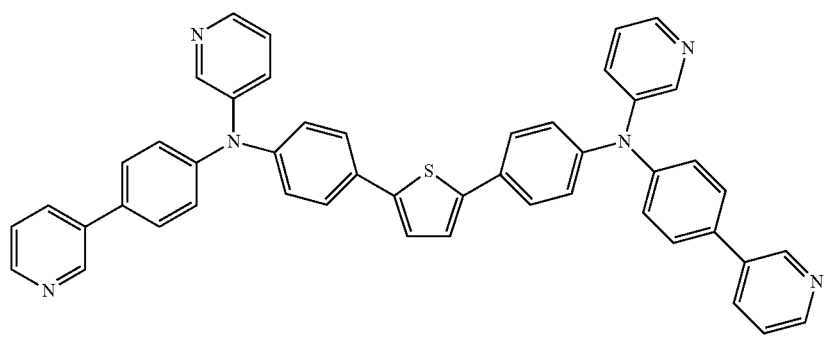
[11]
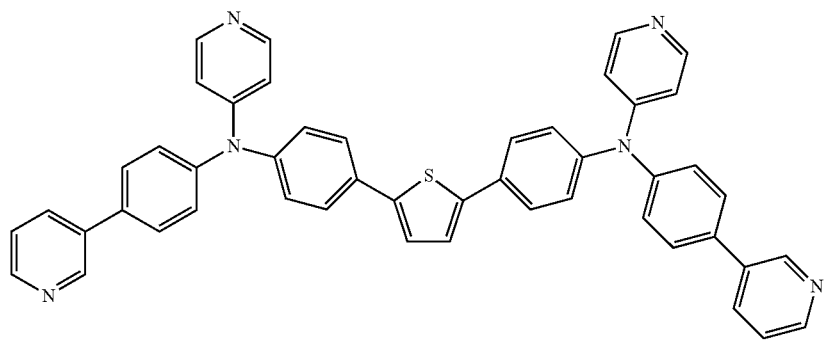
[12]

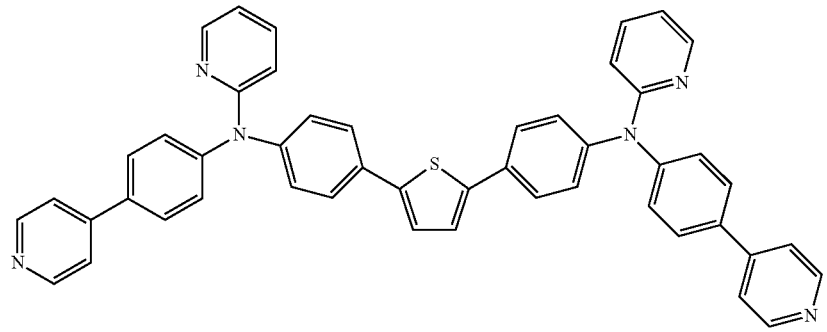
[13]
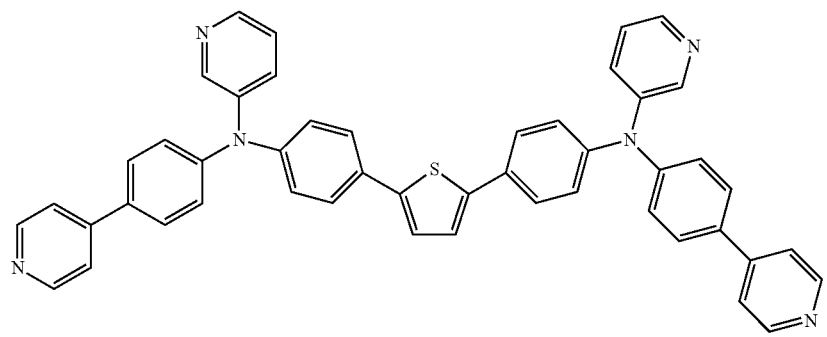
[14]
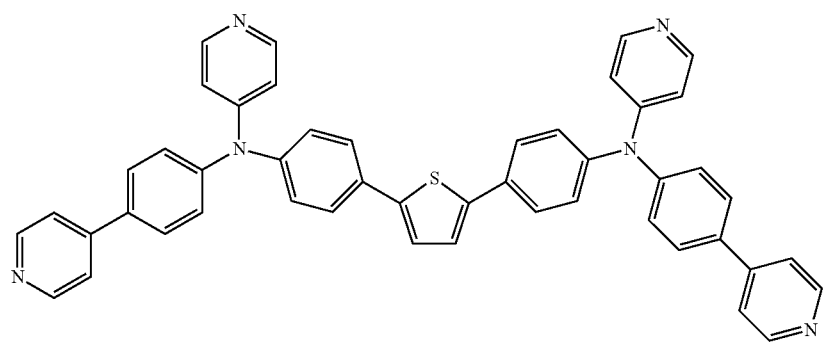
[15]
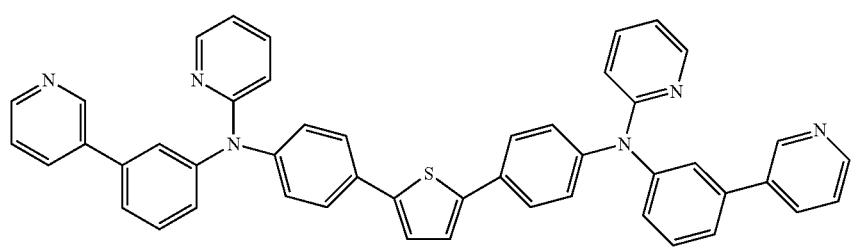
[16]
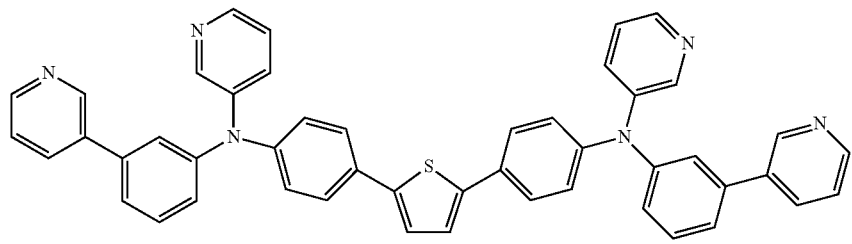
[17]

-continued
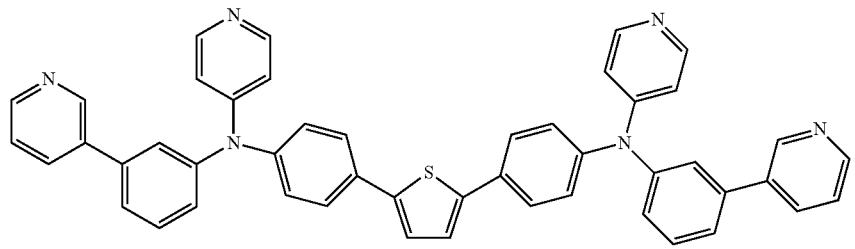
[18]
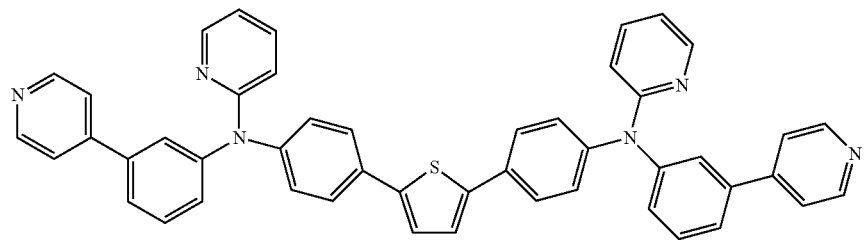
[19]
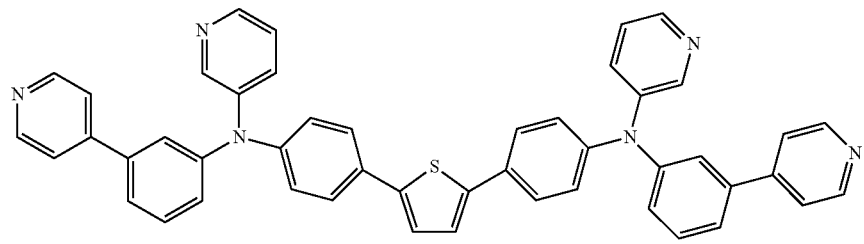
[20]
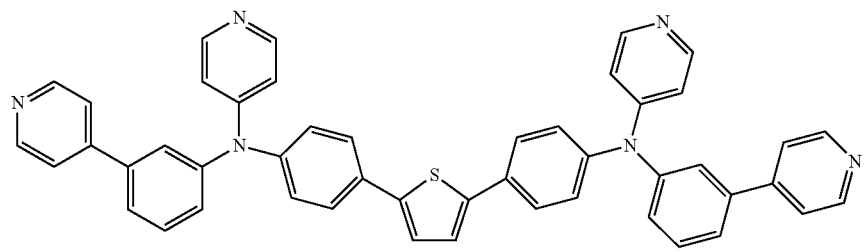
[21]
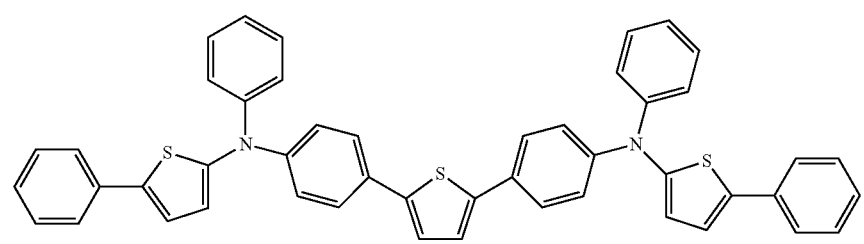
[22]
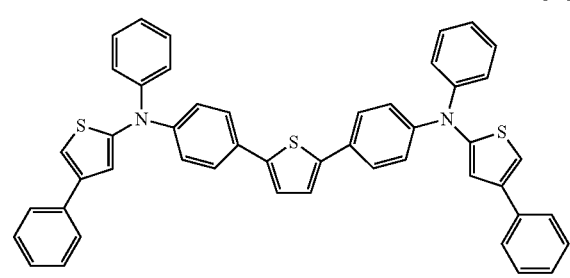
[23]
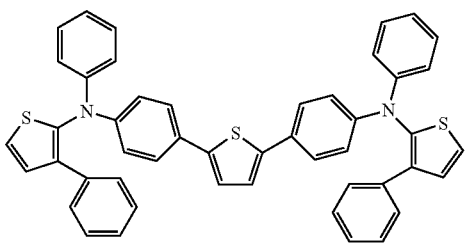
[24]

-continued
[25]
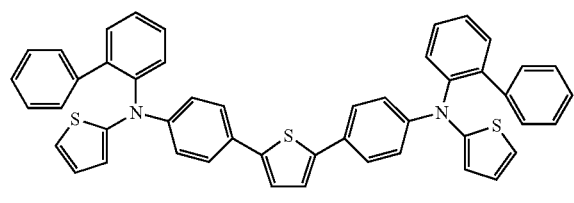
[26]
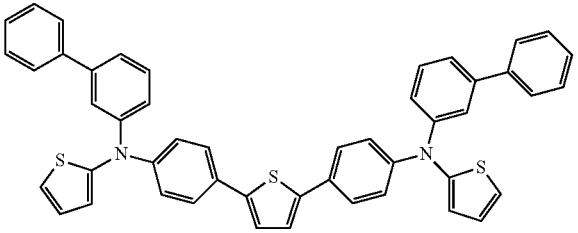
[27]
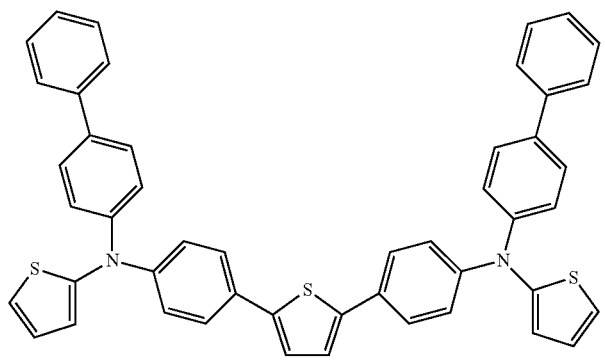
[28]
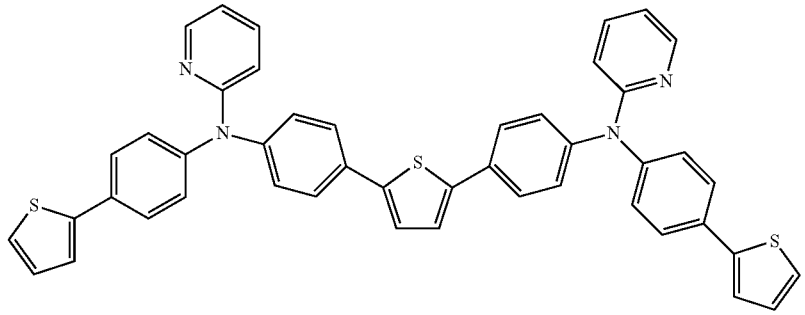
[29]
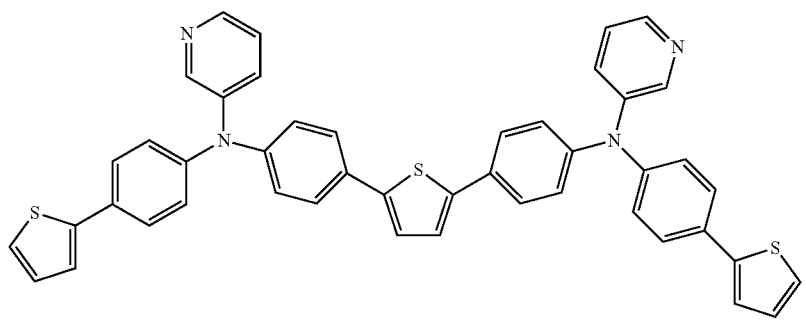
[30]
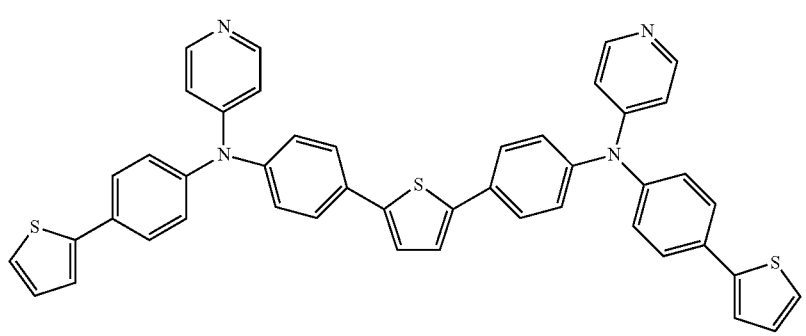

-continued
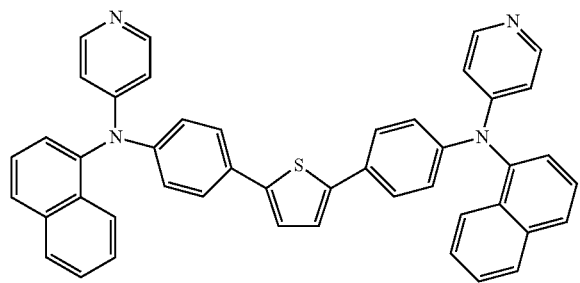
[31]
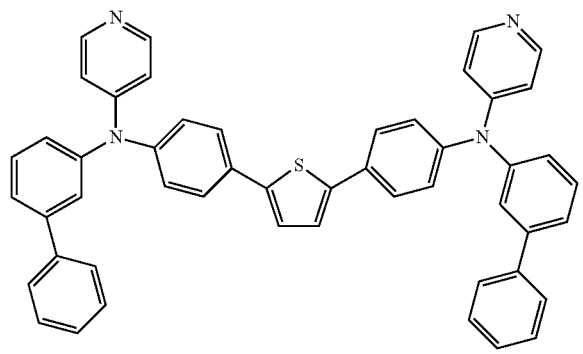
[32]
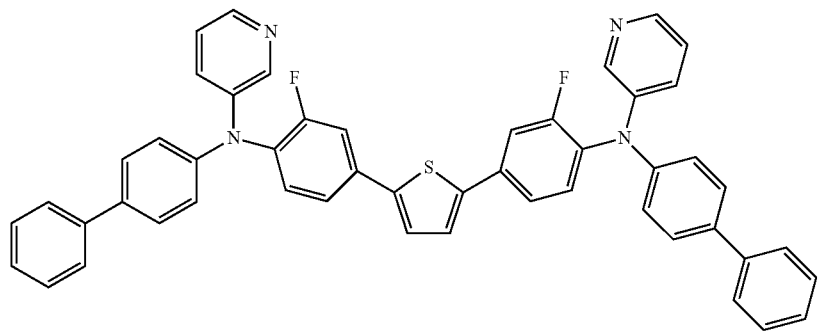
[33]
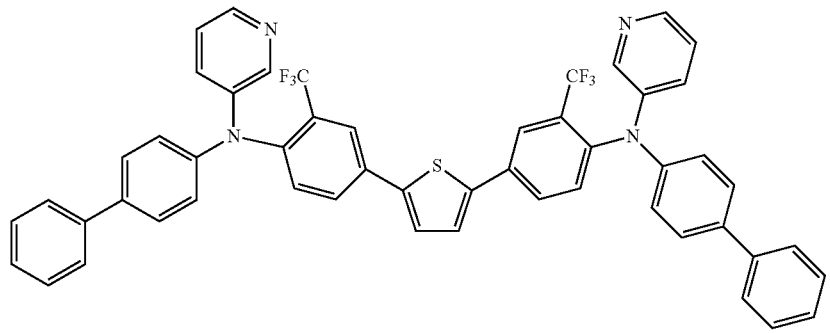
[34]
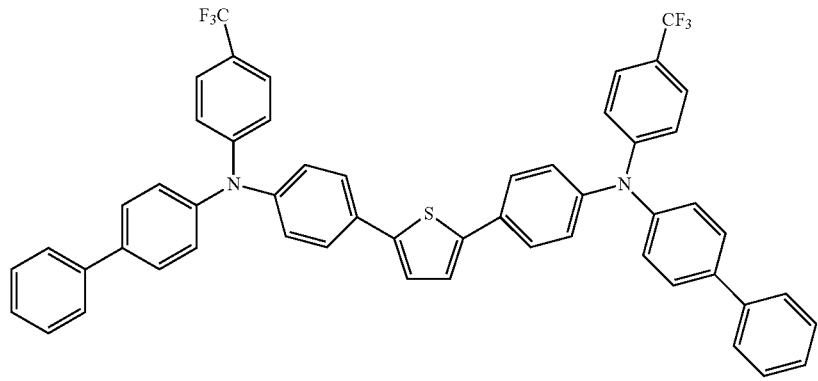
[35]

-continued
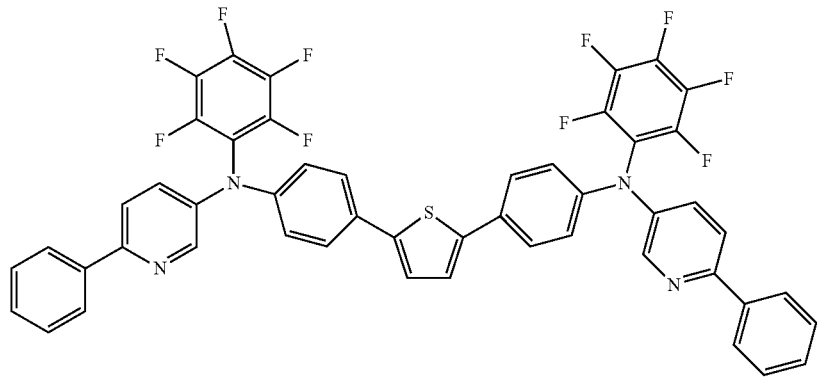
[36]
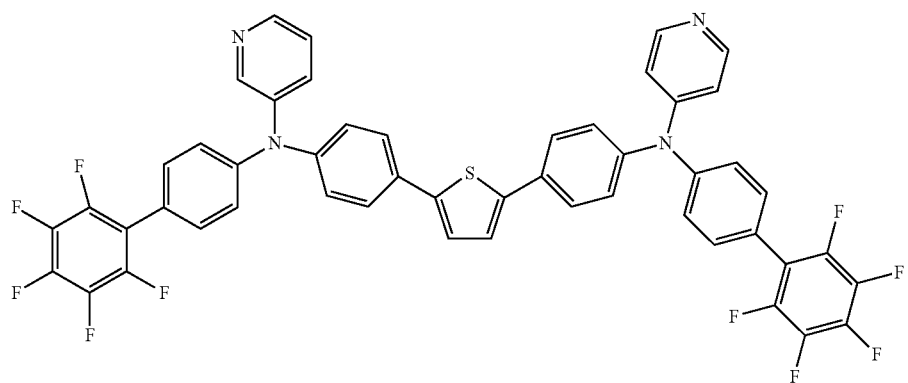
[37]
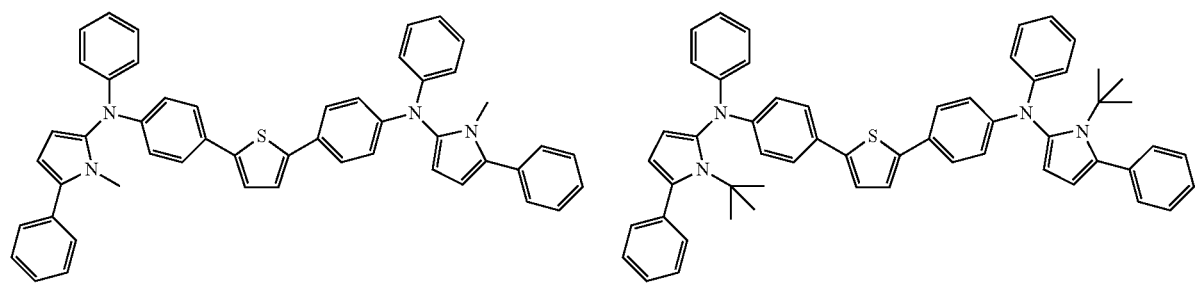
[38]  [39]
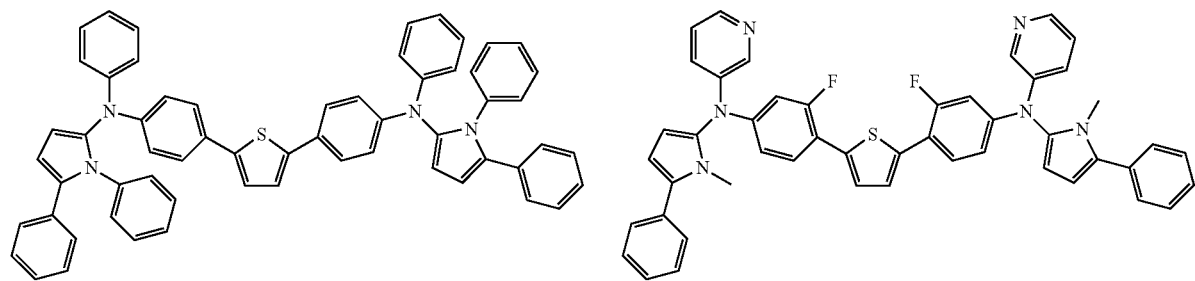
[40]  [41]

-continued
[42]
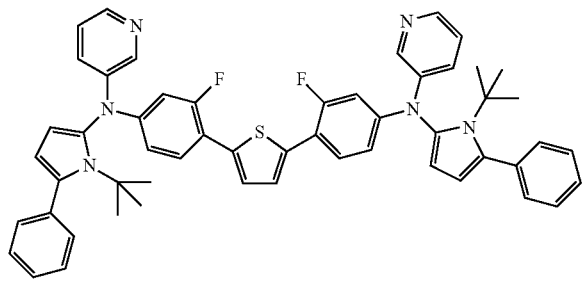
[43]
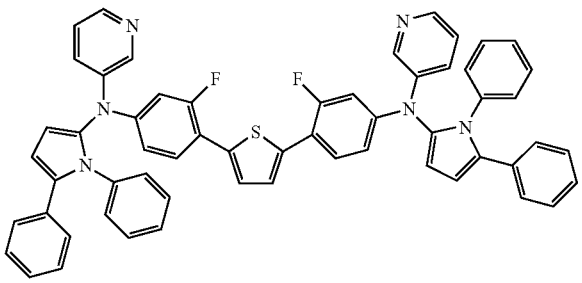
[44]
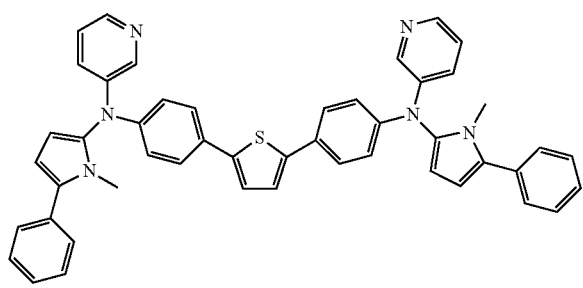
[45]
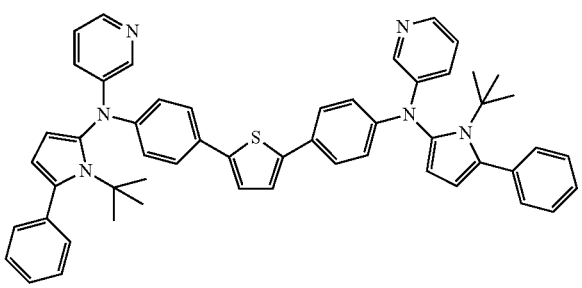
[46]
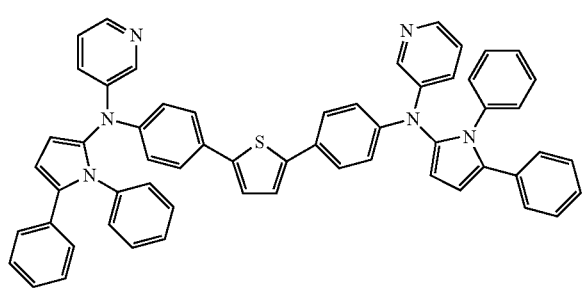
[47]
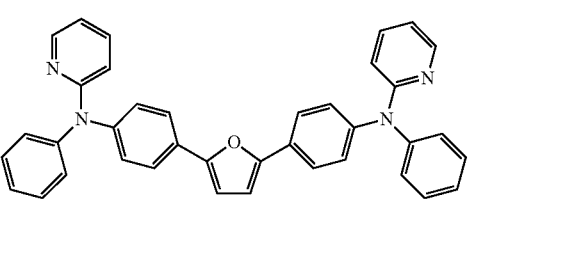
[48]
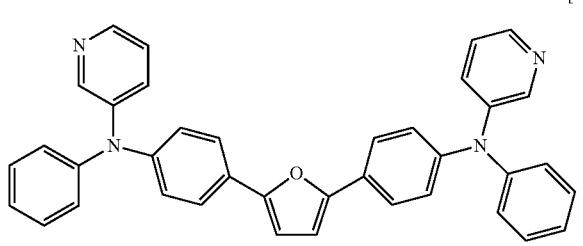
[49]
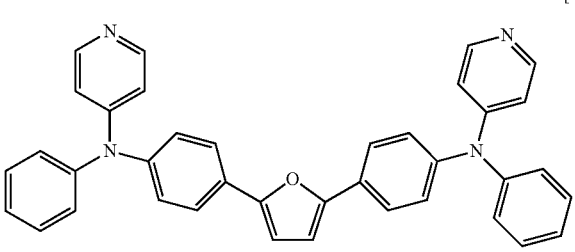
[50]
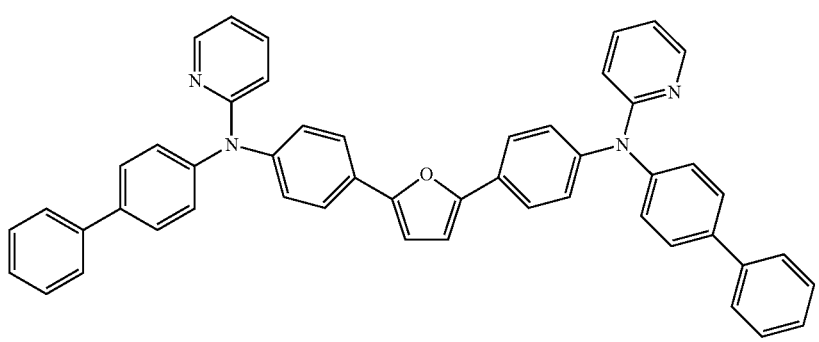

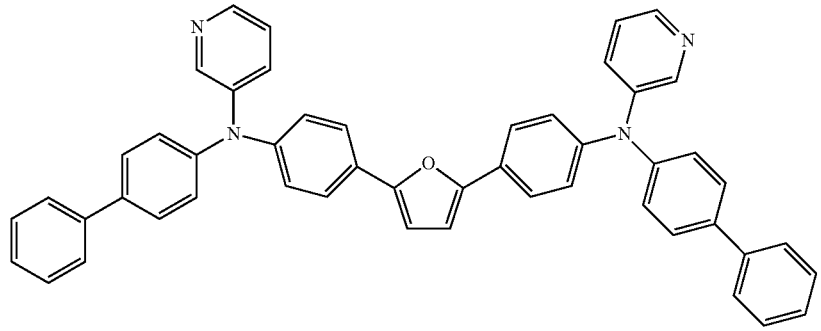
[51]
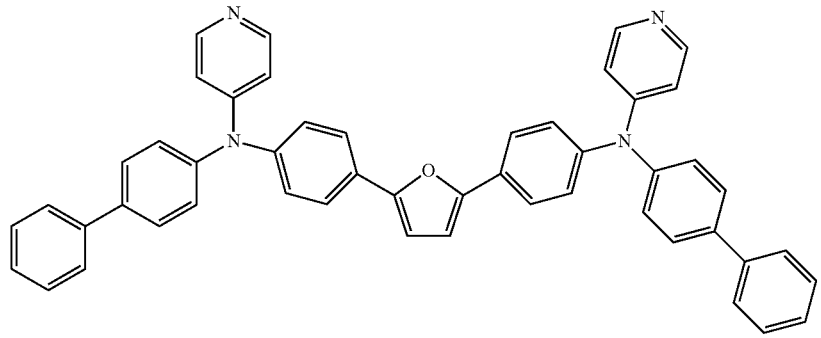
[52]
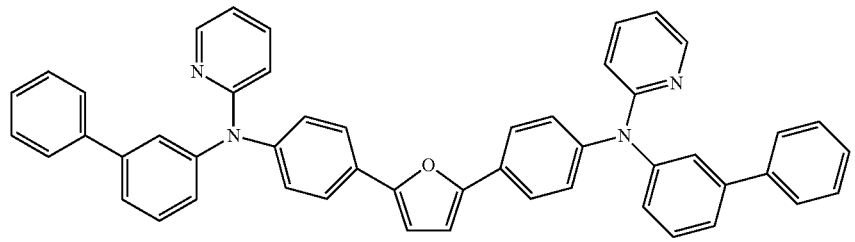
[53]
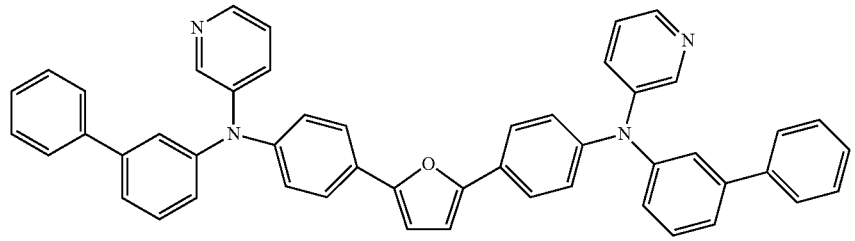
[54]
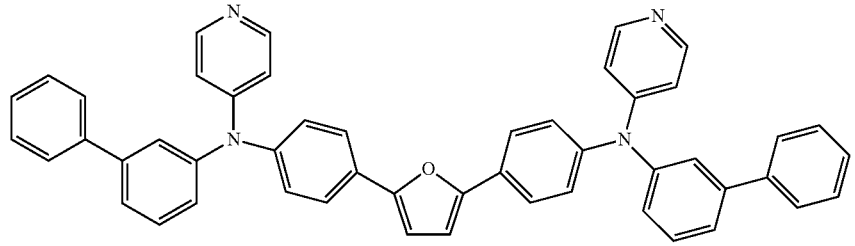
[55]

-continued
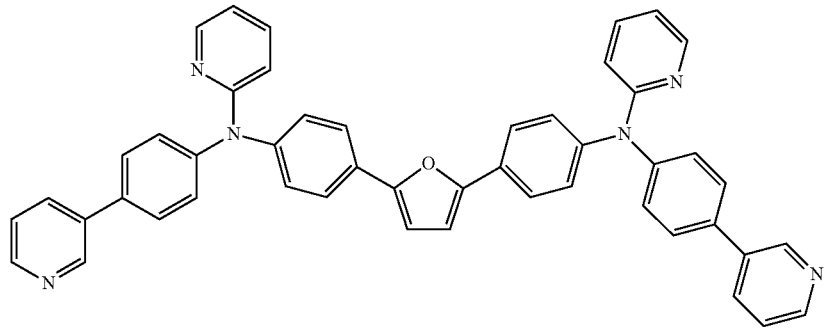
[56]
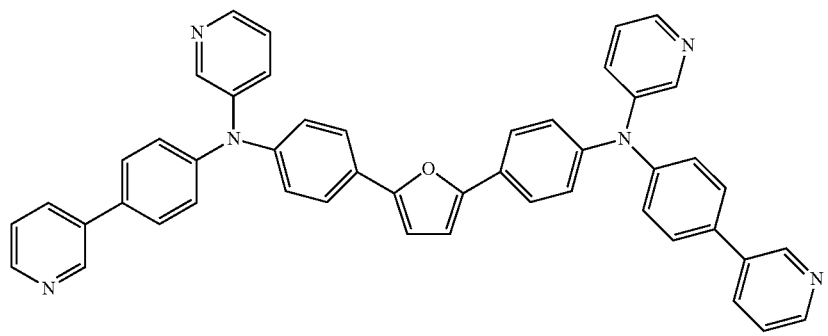
[57]
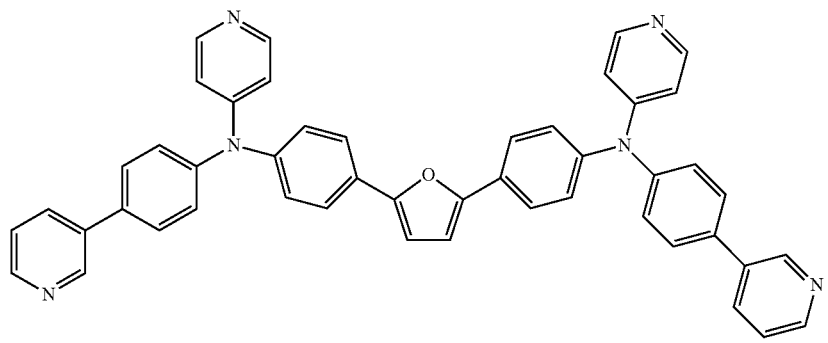
[58]
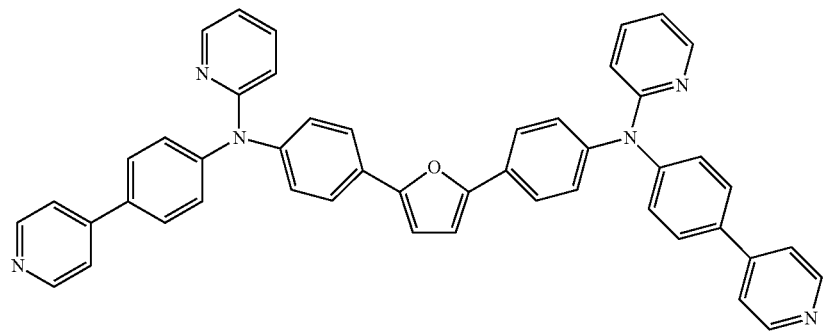
[59]

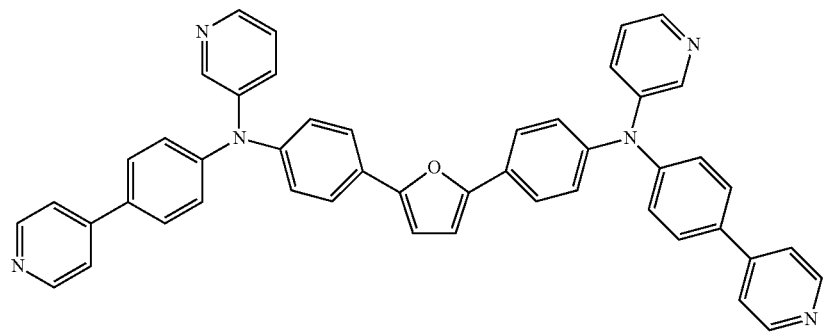
[60]
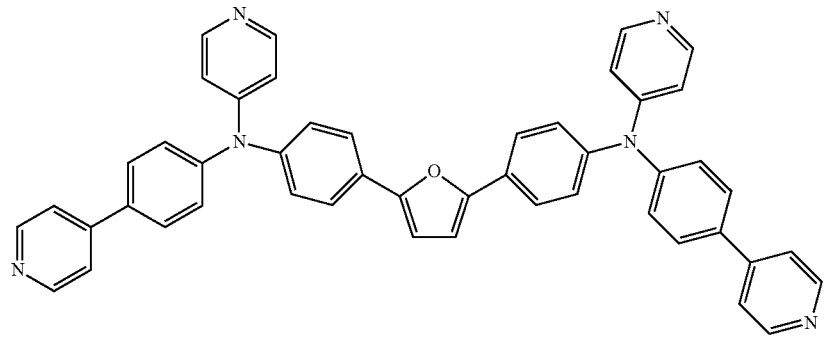
[61]
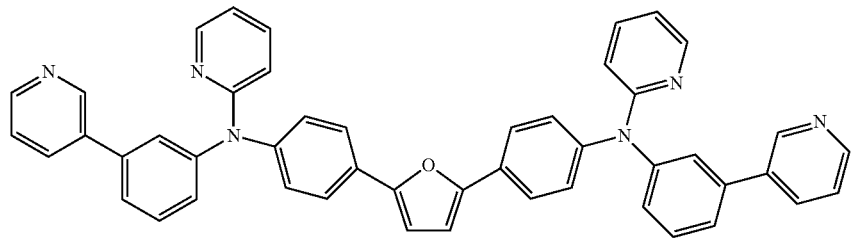
[62]
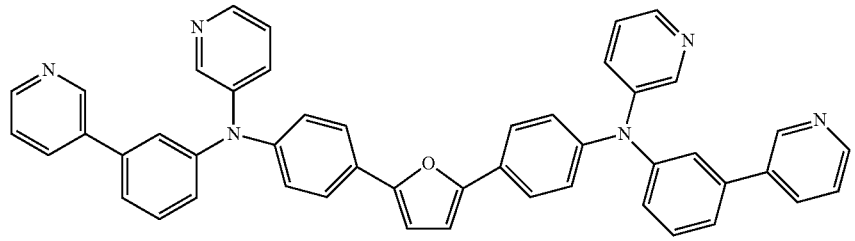
[63]
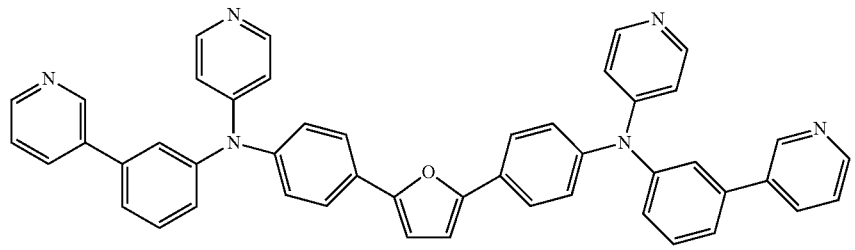
[64]

-continued
[65]
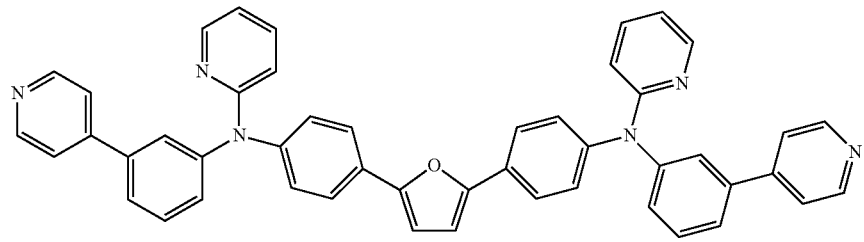
[66]
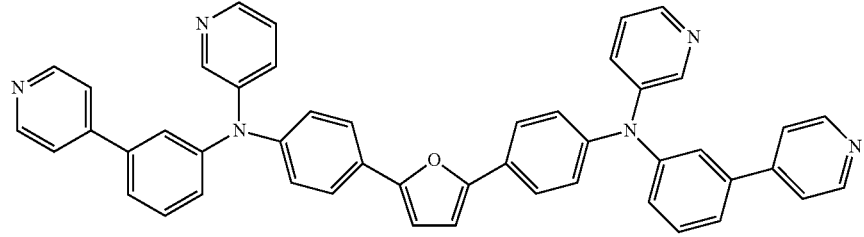
[67]
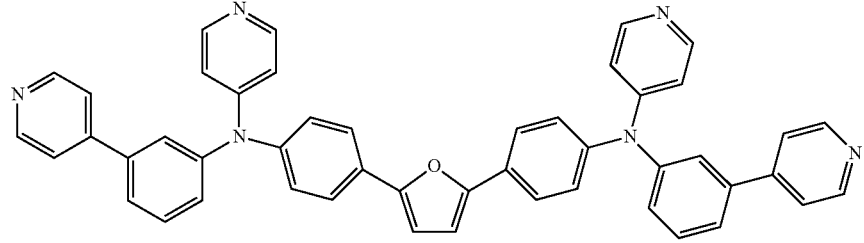
[68]
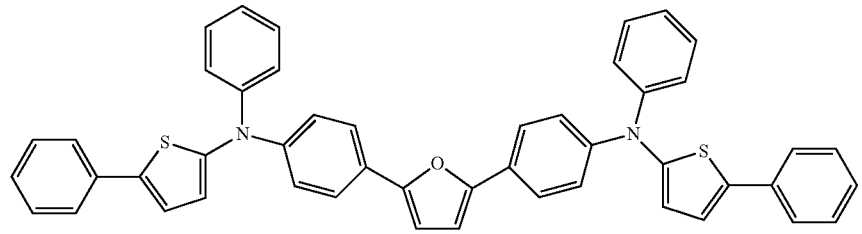
[69]
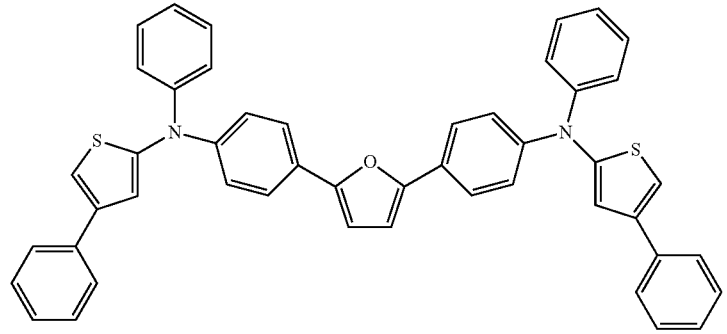
[70]
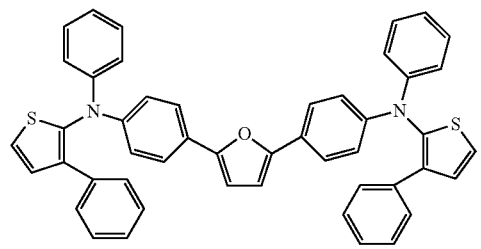
[71]
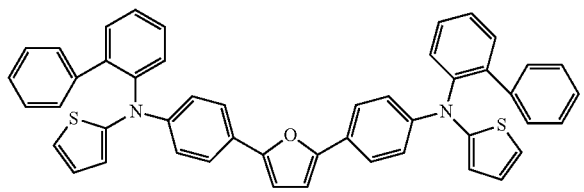

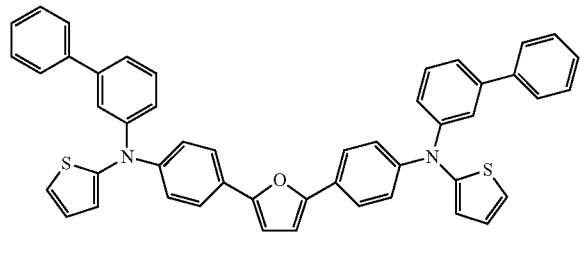
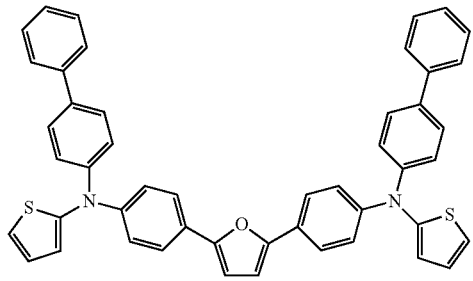
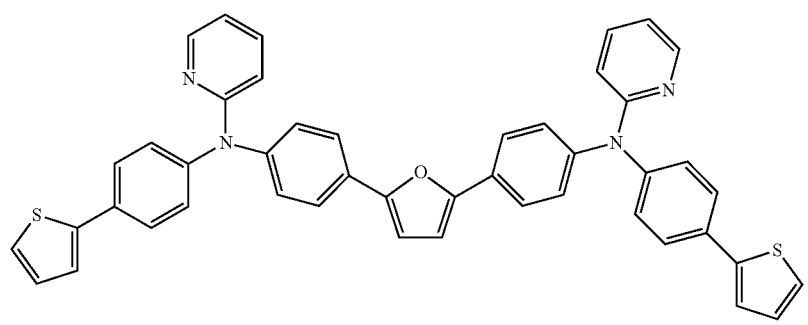
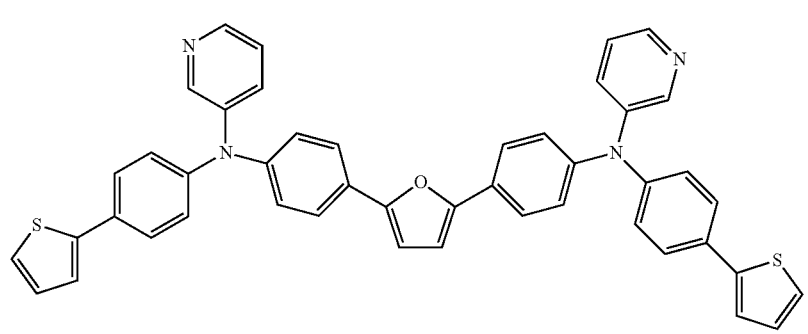
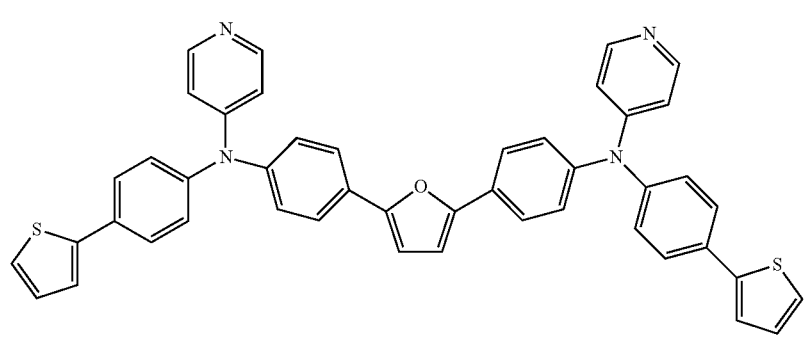

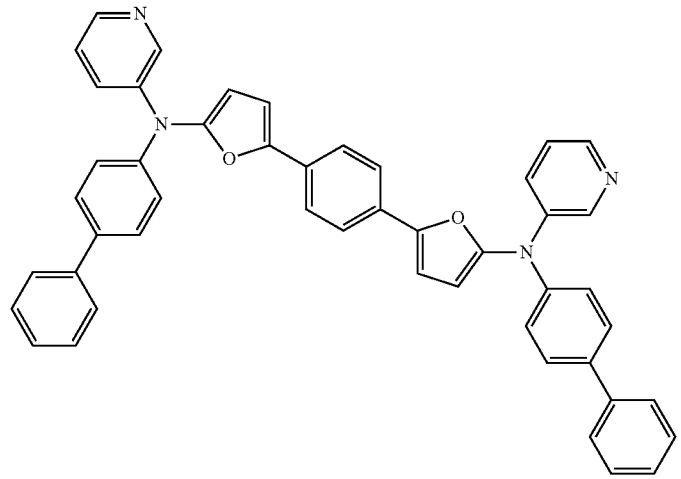
[77]
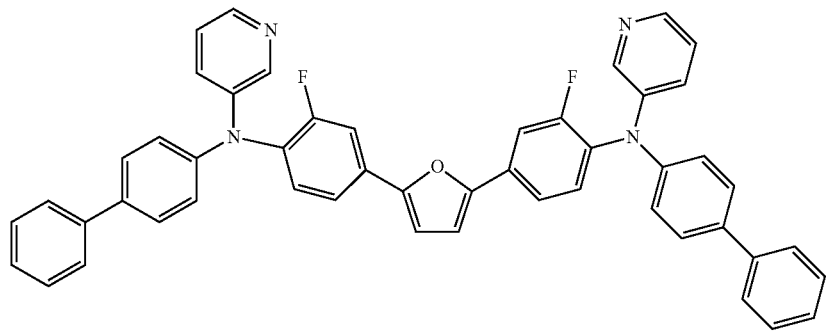
[78]
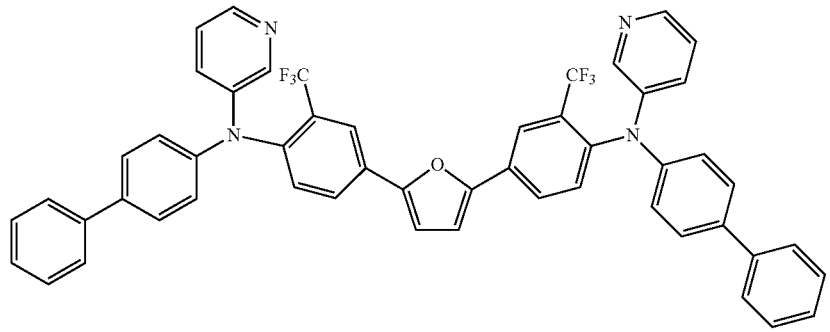
[79]
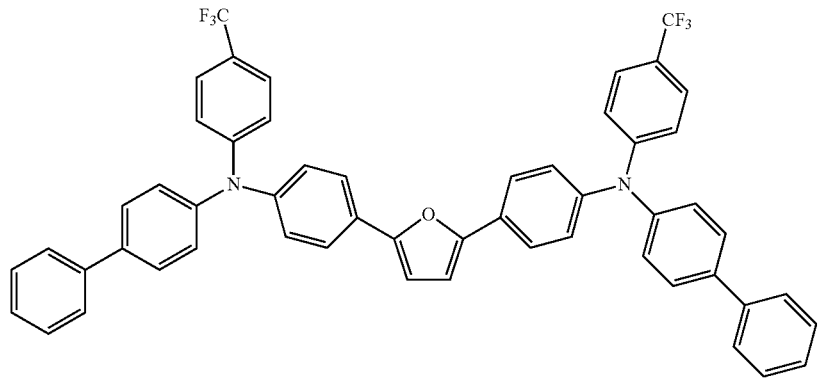
[80]

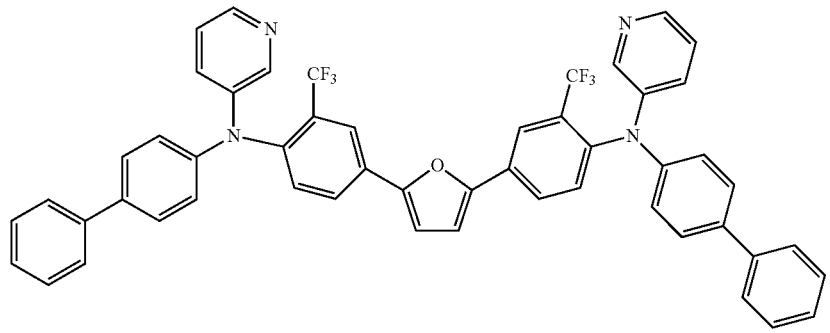
[81]
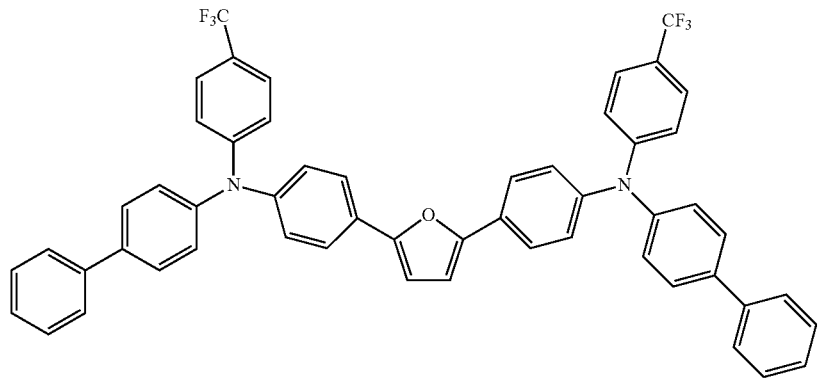
[82]
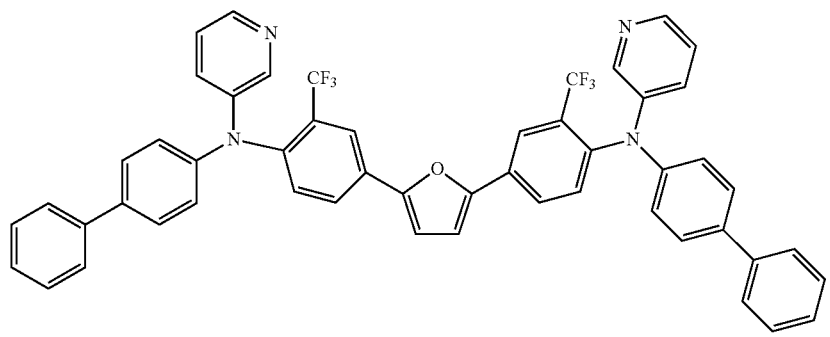
[83]
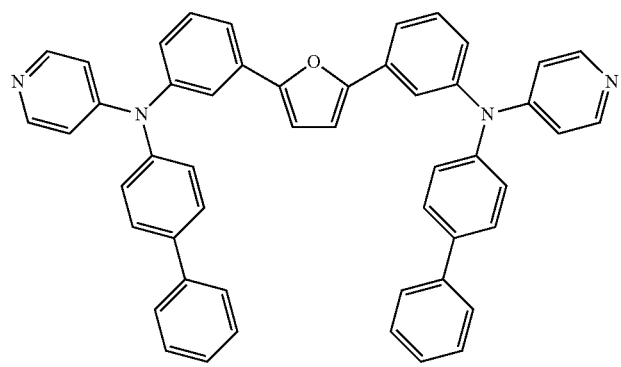
[84]

-continued
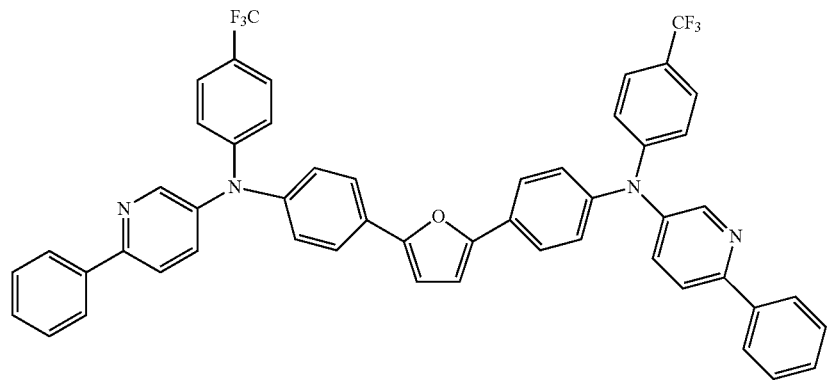
[85]
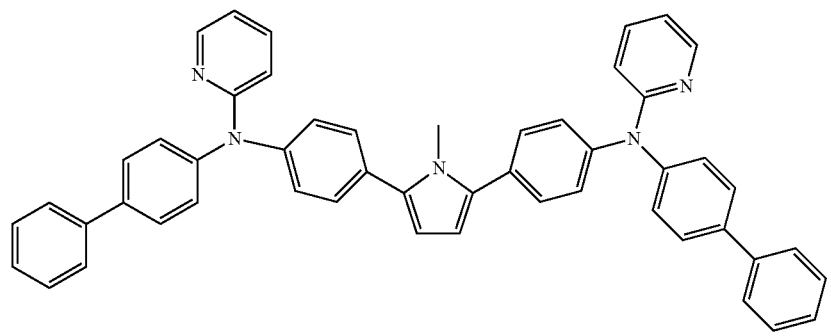
[86]
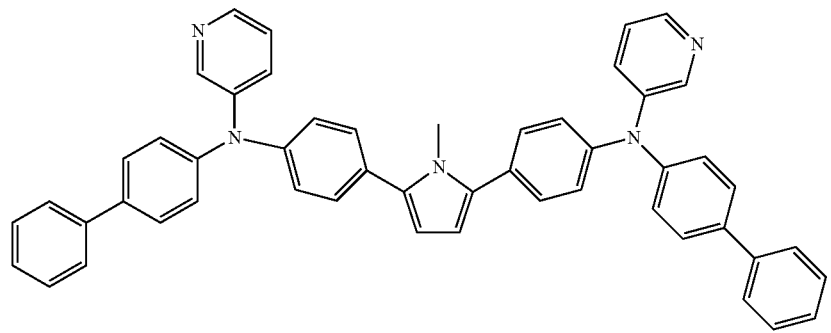
[87]
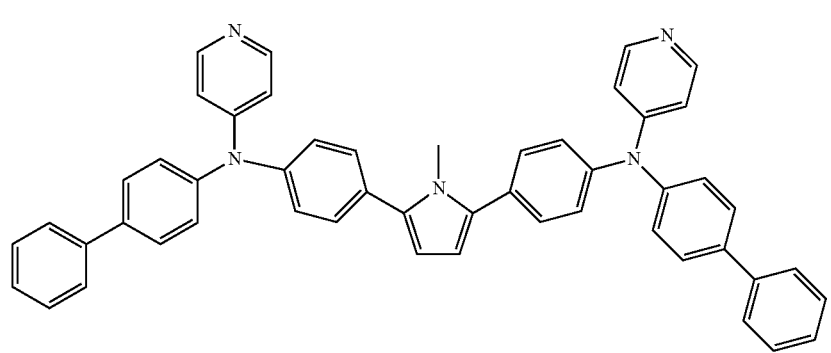
[88]

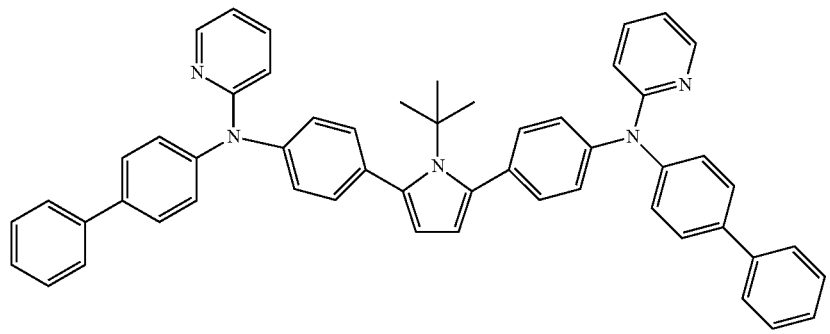
[89]
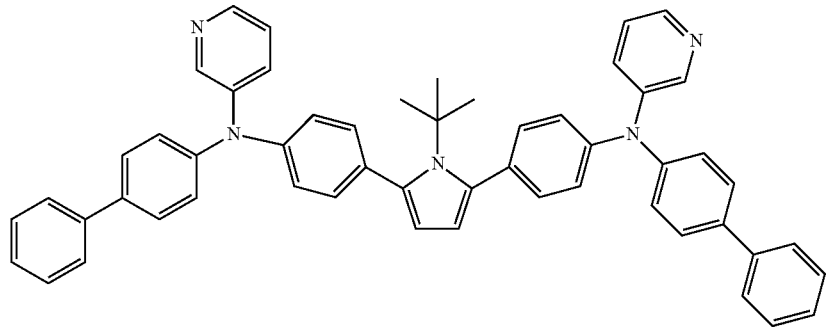
[90]
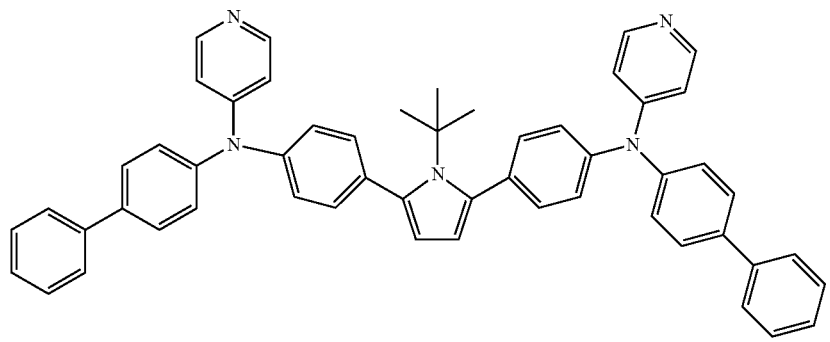
[91]
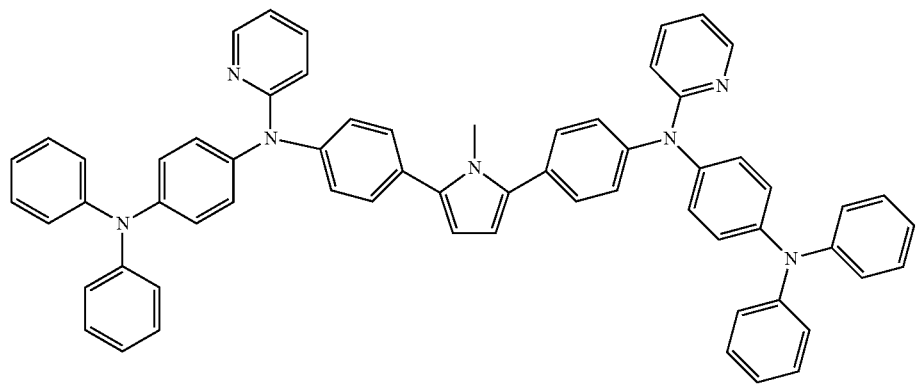
[92]

-continued
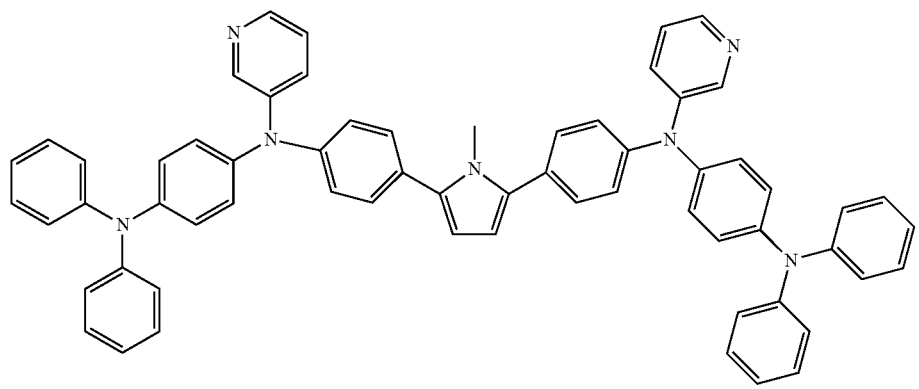
[93]
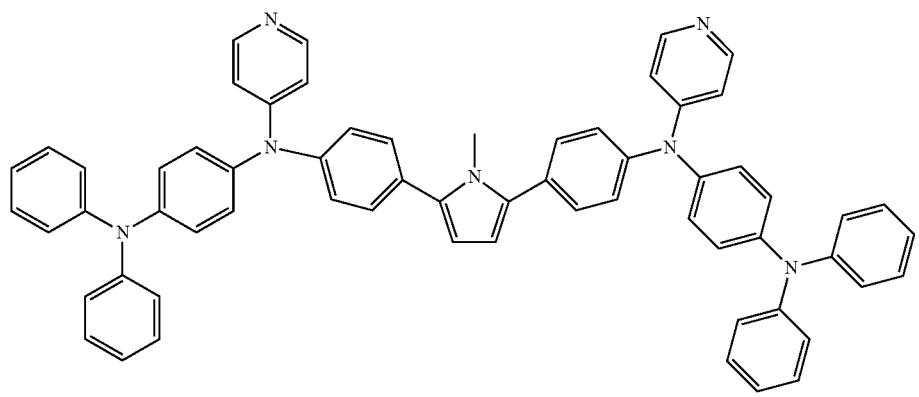
[94]
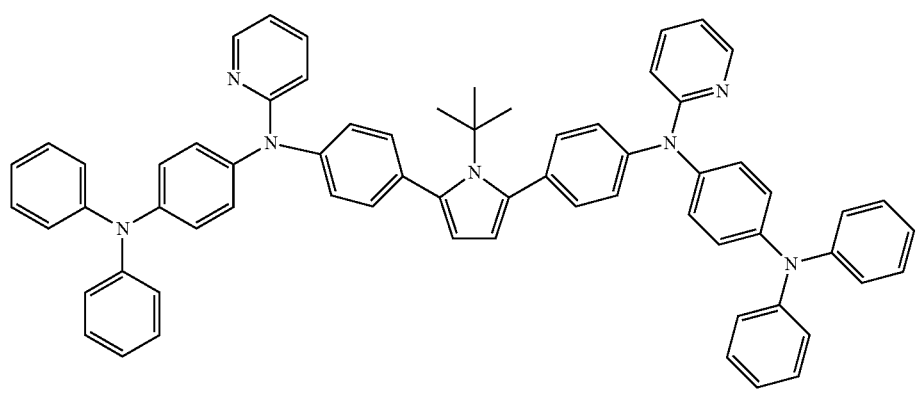
[95]
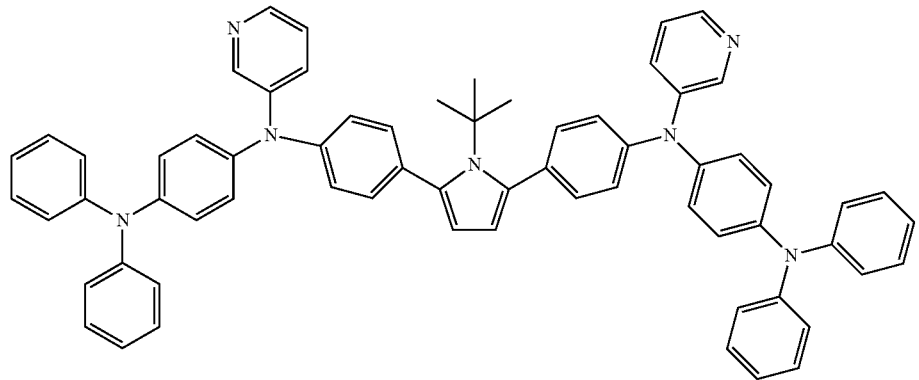
[96]

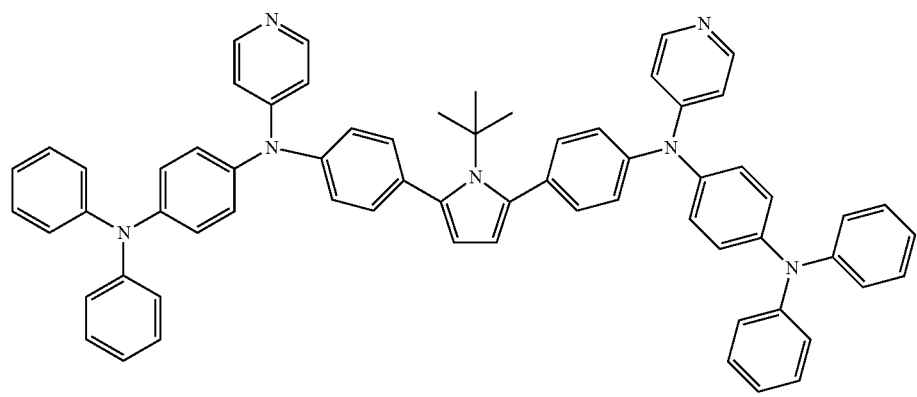
[97]
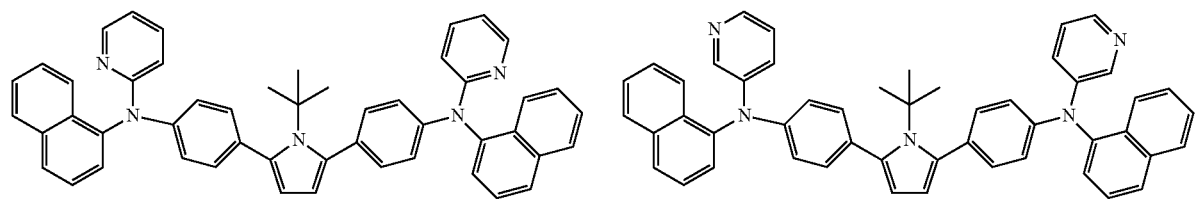
[98] [99]
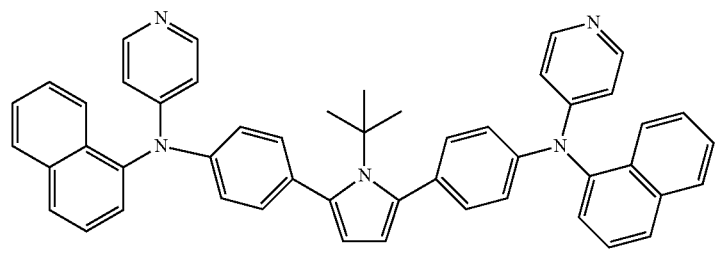
[100]
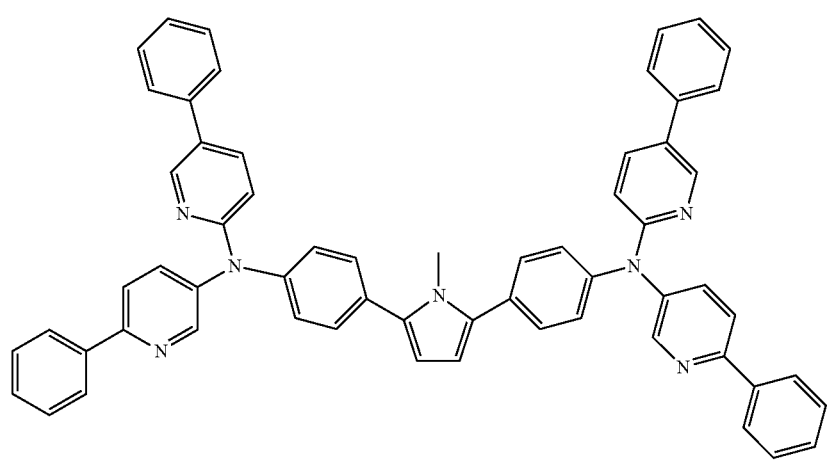
[101]

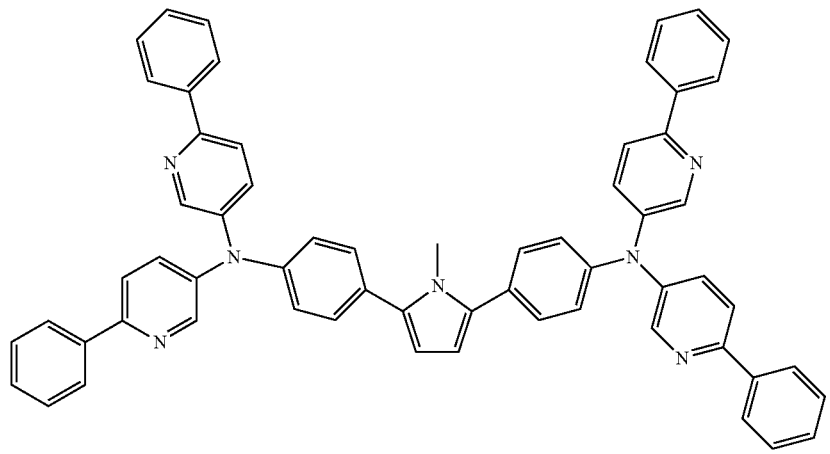
[102]
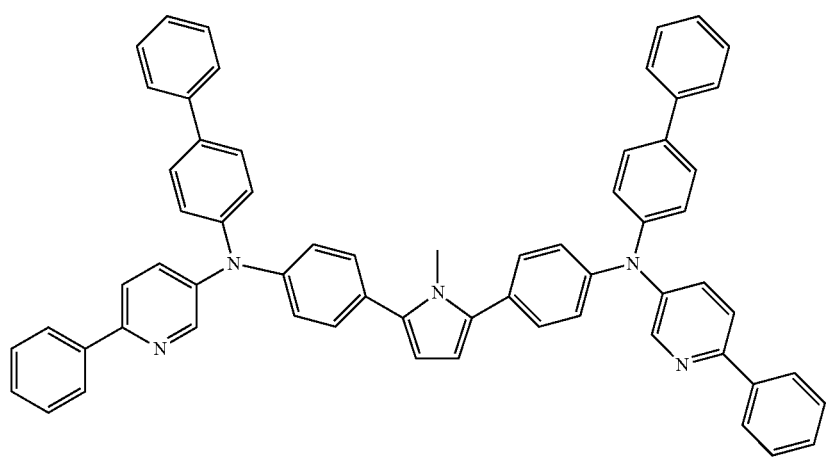
[103]
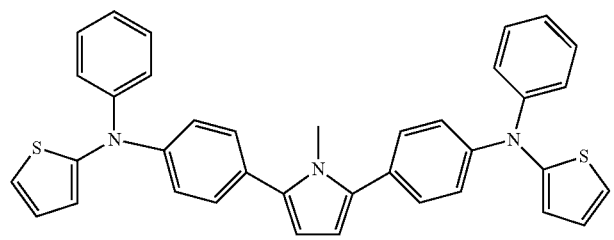
[104]
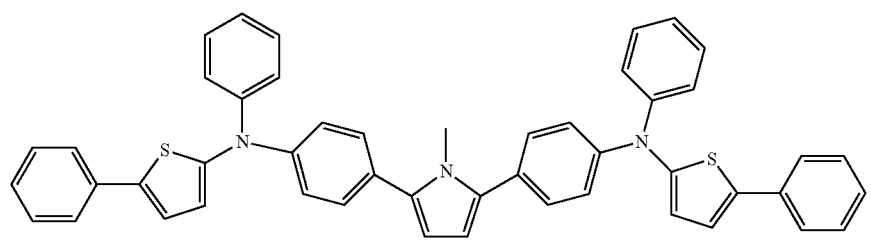
[105]

-continued
[106]
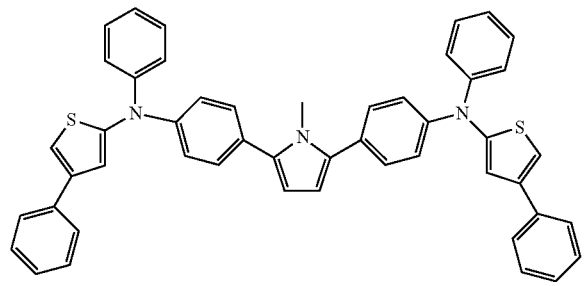
[107]
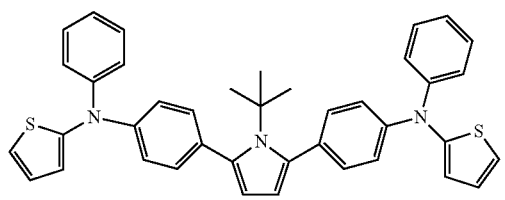
[108]
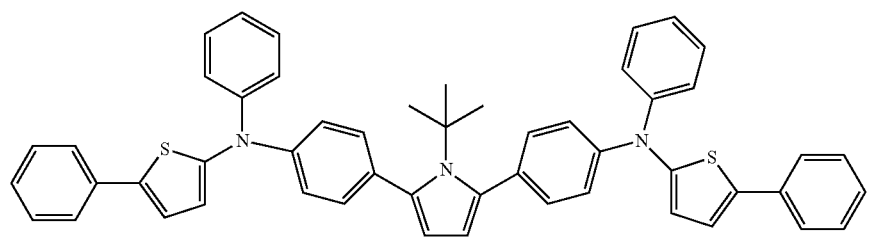
[109]
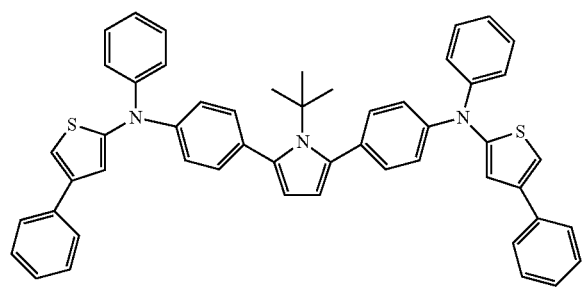
[110]
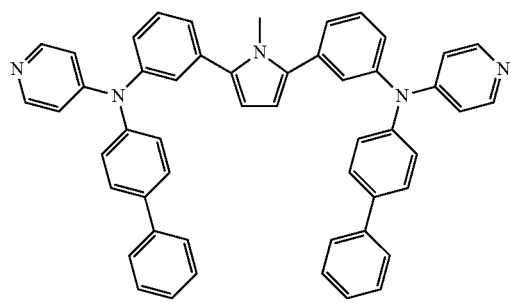
[111]
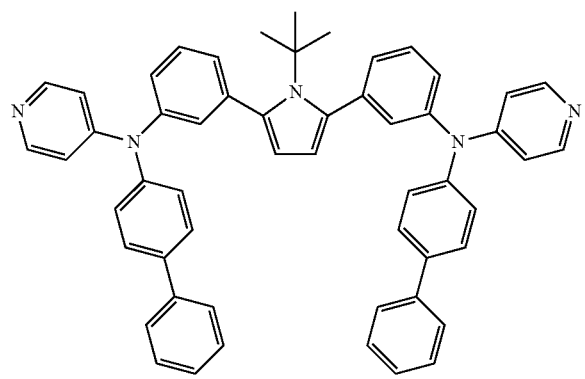
[112]
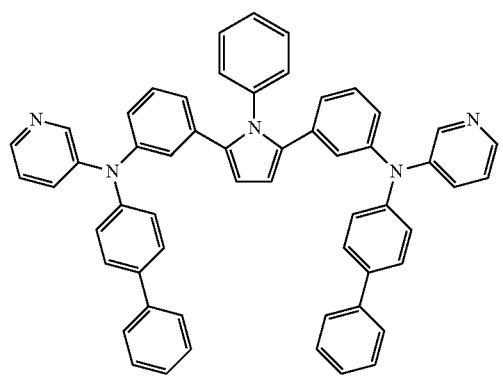

-continued
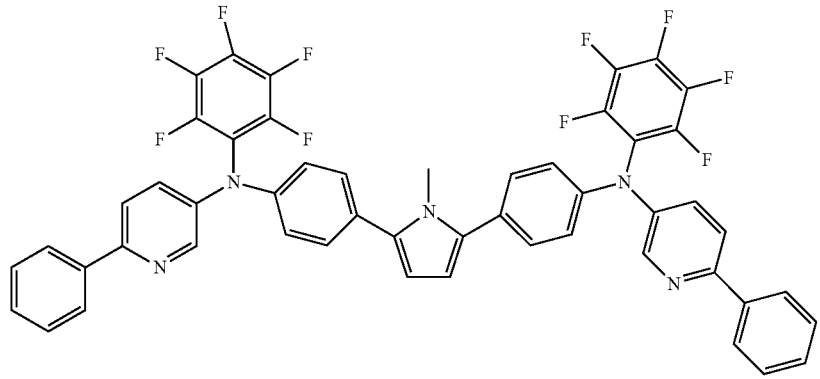
[113]
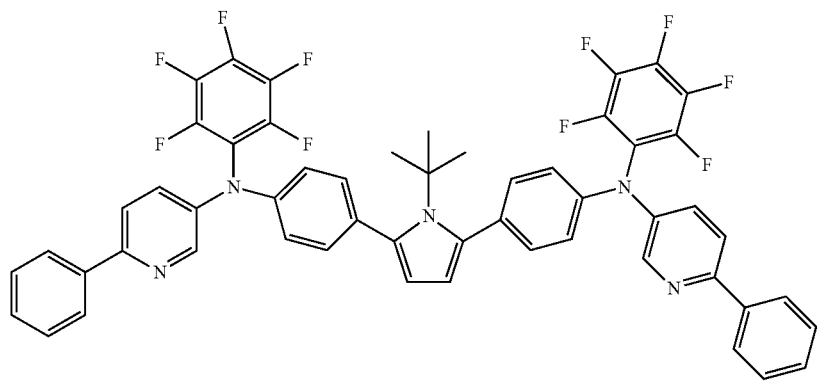
[114]
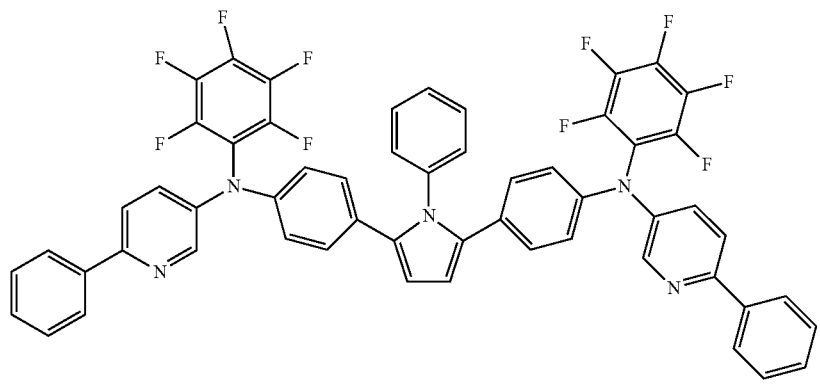
[115]
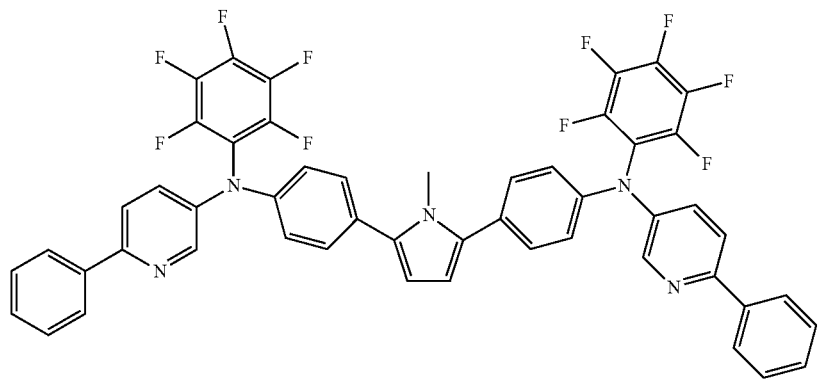
[116]

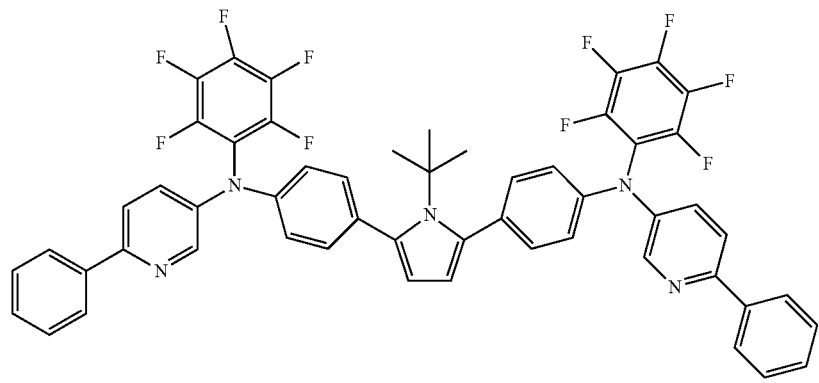
[117]
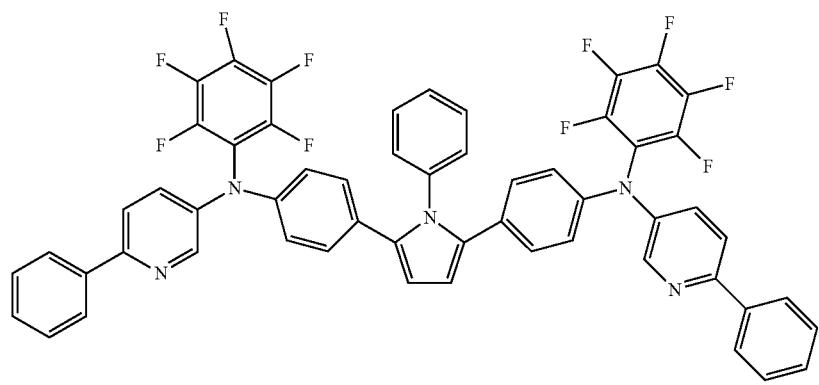
[118]
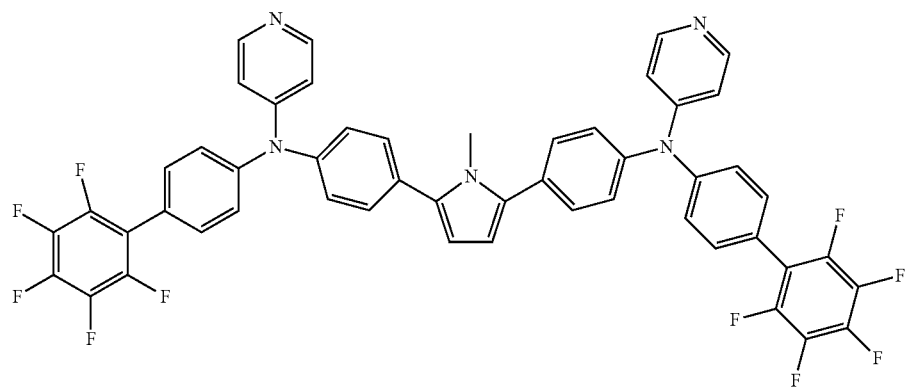
[119]
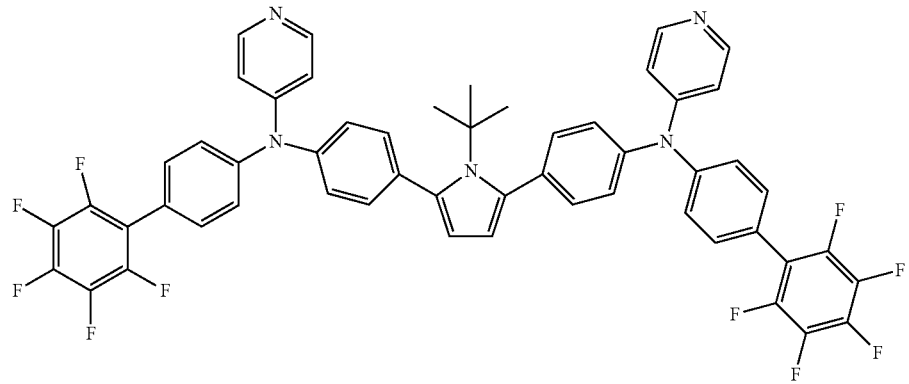
[120]

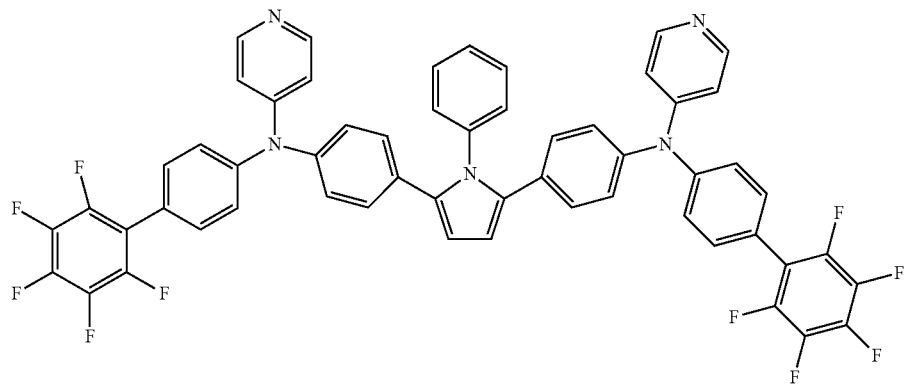
[121]
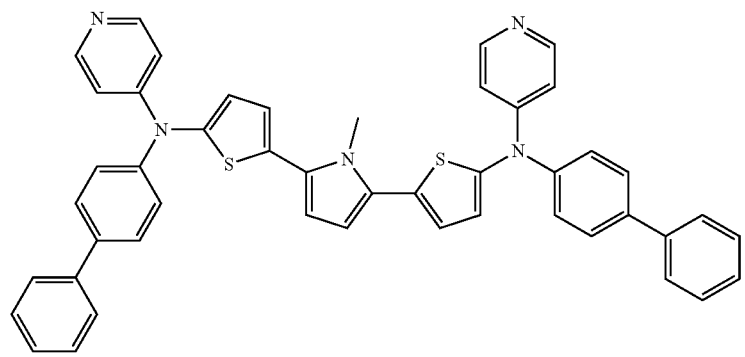
[122]
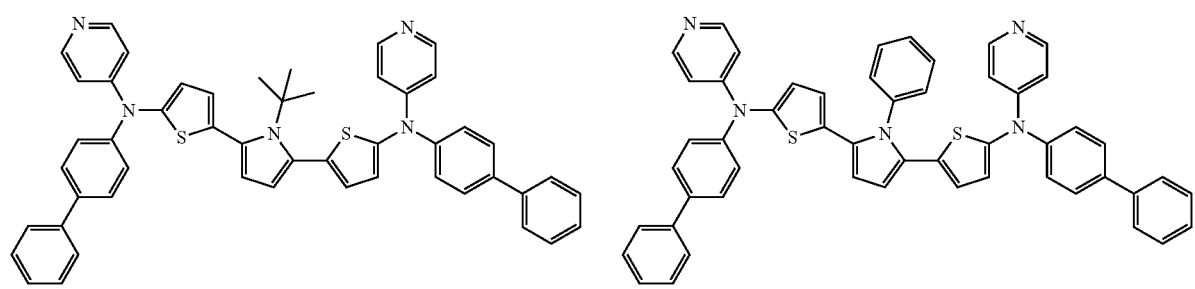
[123] [124]
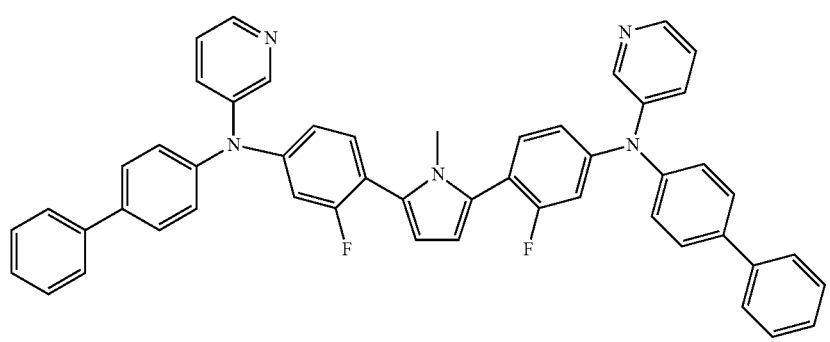
[125]

-continued
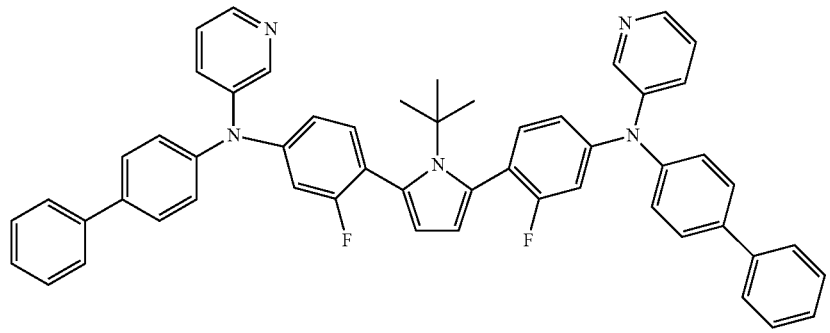
[126]
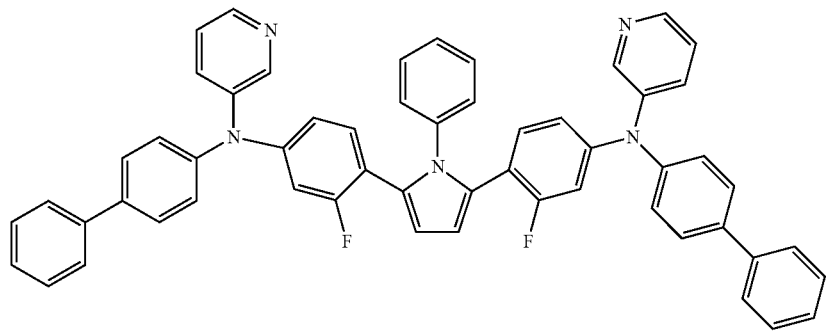
[127]
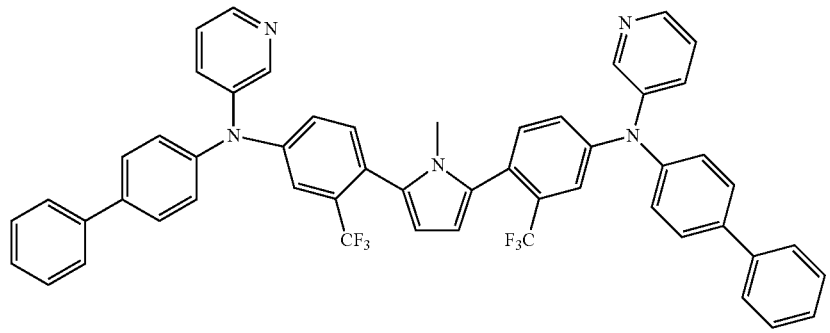
[128]
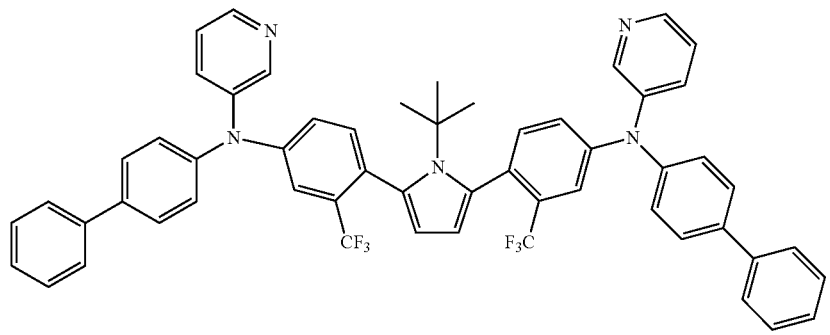
[129]

-continued
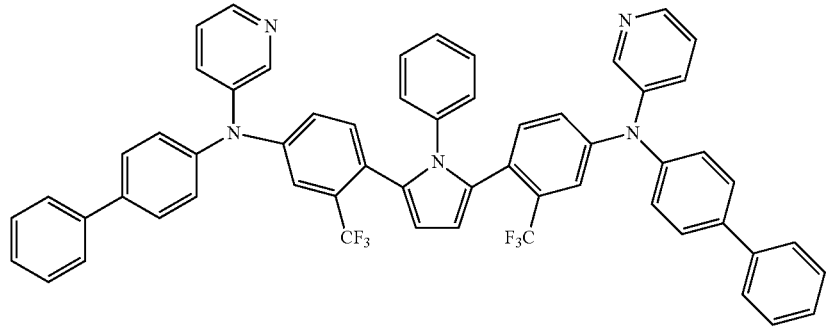
[130]
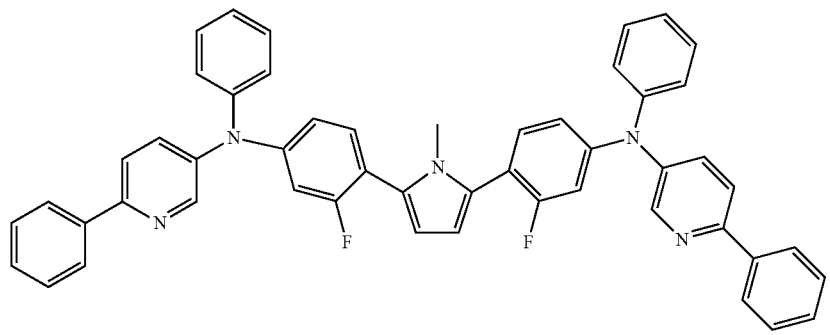
[131]
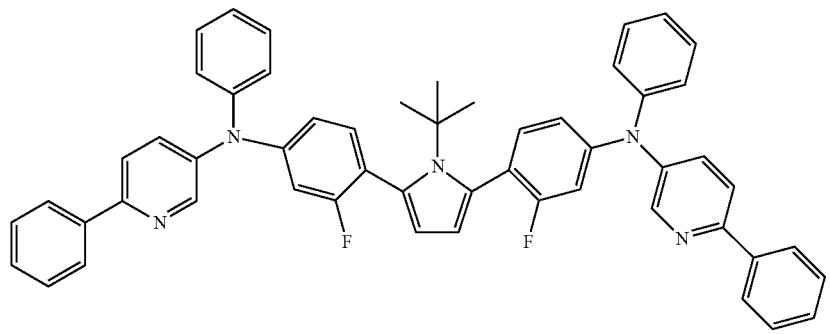
[132]
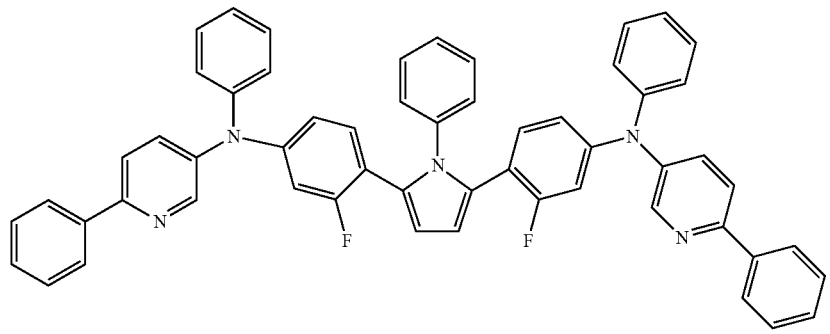
[133]

-continued
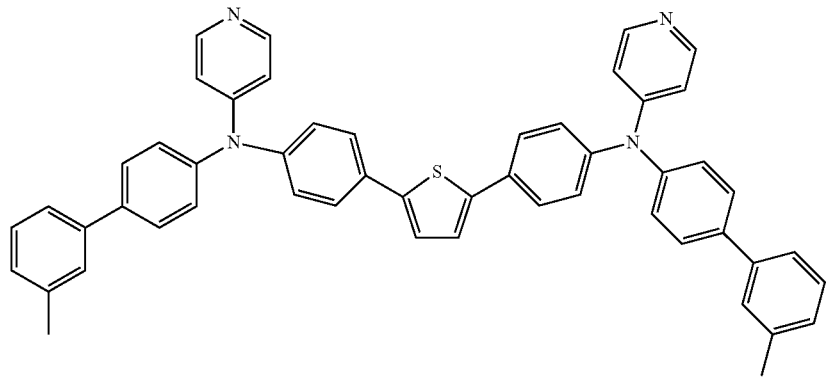
[134]
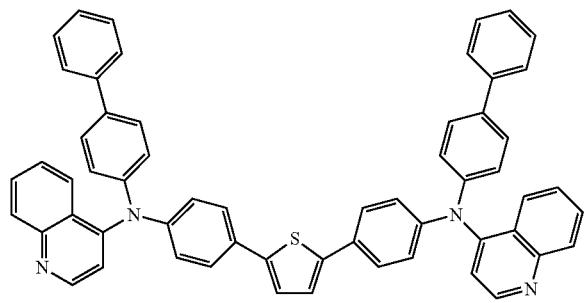
[135]
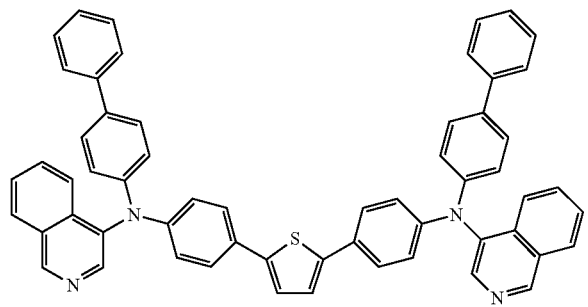
[136]
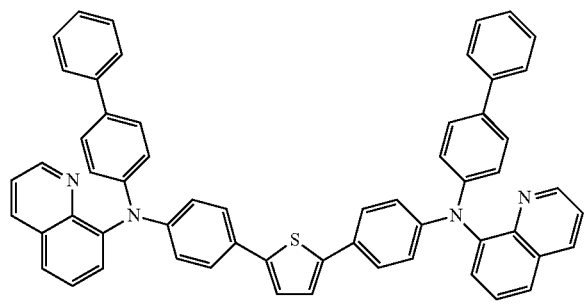
[137]
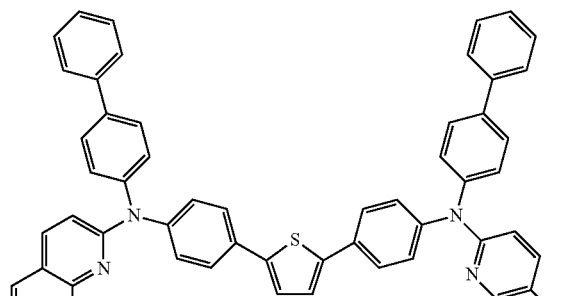
[138]
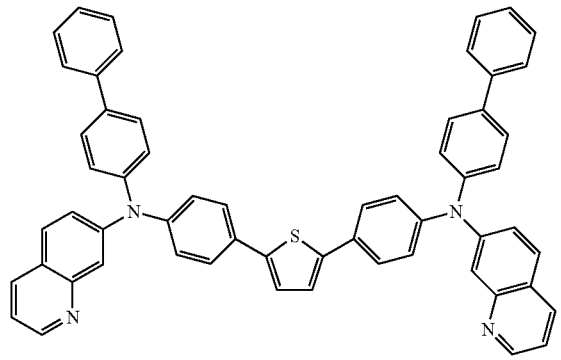
[139]
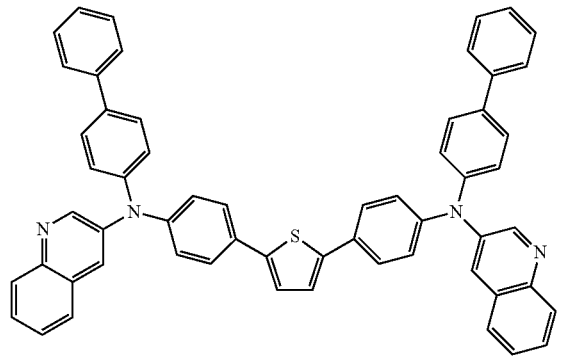
[140]

-continued

[141]
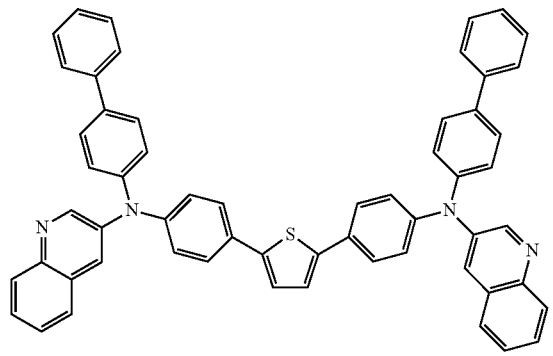

[142]
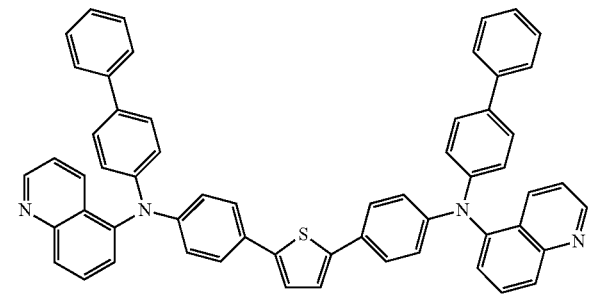

[143]
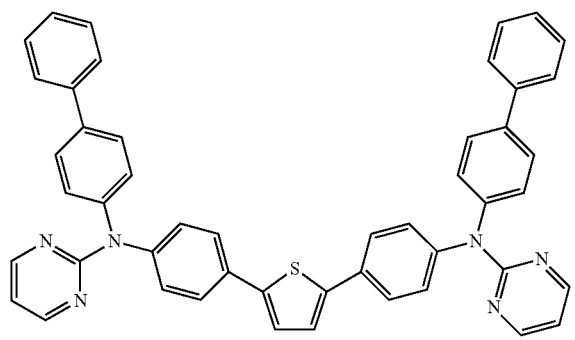

[144]
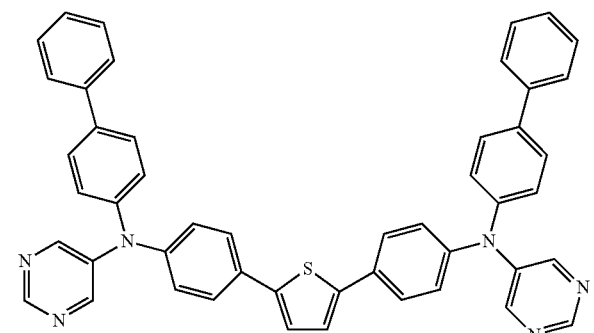

[145]
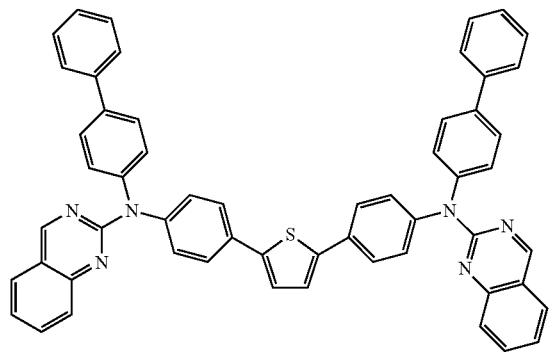

[146]
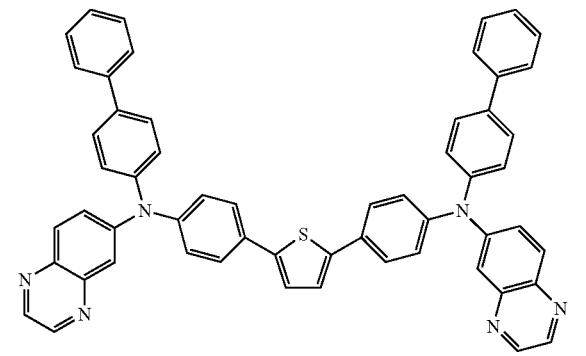

Synthesis of the aromatic amine compound of Formula (1) may be achieved by any known method, such as the cross coupling reaction of transition metal such as nickel and palladium.

In the following reaction equation, M is the Kumada-Tamao Coupling Reaction of magnesium compounds represented by MgBr, etc., the Negishi Coupling Reaction of zinc compounds represented by ZnCl etc., the Migita-Kosugi-Stille Coupling Reaction of tin compounds represented by SuBu3 etc., the Hiyamai Coupling Reaction of silicon compounds represented by Si(OH)3 etc., and the Suzuki-Miyaura Coupling Reaction of compounds represented by B(OH)2 etc., without limitation. Hal denotes halogens such as a chlorine atom, a bromine atom and an iodine atom or pseudohalogens such as trifluoromethanesulfo etc. Among these reactions, the Suzuki-Miyaura Coupling Reaction is preferred because the materials of this reaction are main-group metal compounds that have low toxicity, the reaction generates fewer by-products, and it is easy to remove the unreacted main-group metal compounds.

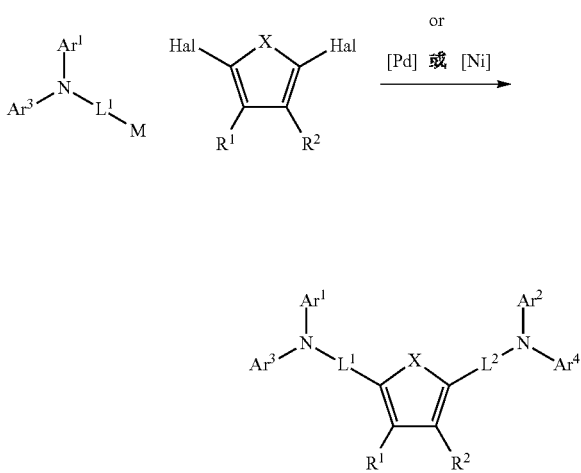

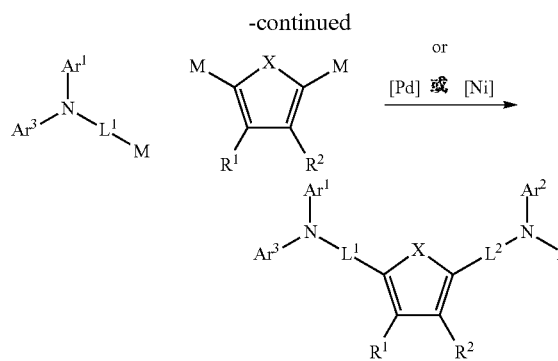

The other synthesis methods use C—N bonding of transition metals such as nickel, palladium and copper to perform reaction. For example, the Buchwald-Hartwig Reaction using nickel or palladium and the Ullman Reaction using copper may be used, but is not limited to these methods. Among these reactions the Buchwald-Hartwig Reaction is preferred because the condition is mild and it has superior selectivity of the functional groups. While $Ar^1$, $Ar^2$ or $Ar^3$, $Ar^4$ are different substituents, according to the theoretical mix ratio of amine and halide, synthesis is performed by stages. The disclosed aromatic amine compound of Formula (1) may be used alone or may be mixed with other materials and used in the organic light-emitting element.

Below is the description of the implementation of the disclosed organic light-emitting element. The present invention provides an organic light-emitting element that contains an aromatic amine compound. The organic light-emitting element has a substrate, a first electrode, one layer or more of organic film in which a light-emitting layer is included, a second electrode allowing the light emitted by the light-emitting layer to pass through and a light extraction efficiency improving layer. The light-emitting layer emits light when energized.

In the disclosed light-emitting element of the present invention, the substrate used is preferably a glass substrate such as soda glass, alkali-free glass, etc. The thickness of the glass substrate is not limited as long as it is enough to maintain the mechanical strength of the substrate, such as, for example, 0.5 mm or more. The glass material for the substrate having fewer ions dissolved therefrom is better, and thus the alkali-free glass is preferred. Alternatively, glass with protective coating of $SiO_2$ which is sold in the market may be used. If the first electrode functions stably, the substrate may not necessarily be made of glass. For example, an anode may be formed on a plastic substrate.

The material of the first electrode is preferably made of metals having high refractive index, such as gold, silver, aluminum and metallic alloys such as APC alloys. These metals and metallic alloys may be stacked into multiple layers. Additionally, one or more transparent conducting metallic oxides such as tin oxide, indium oxide and indium tin oxide (ITO), indium zinc oxide (IZO) may be used to cover the upper surface and/or lower surface of theses metals, metallic alloys or their laminates.

The material of the second electrode is preferably made of a material that can form translucent or transparent film pervious to light, such as silver, magnesium, aluminum, calcium or alloys thereof and transparent conducting metallic oxides, such as tin oxide, indium oxide, indium tin oxide (ITO), and indium zinc oxide (IZO). These metals, alloys or metallic oxides may be stacked into multiple layers.

The foregoing electrodes may be made through resistance heating evaporation, electron-beam evaporation, sputtering, ion plating, or adhesive coating, without particular limitation. Moreover, according to the work functions of the materials used in the first electrode and the second electrode, one acts as an anode relative to the organic film layer, and the other acts as a cathode.

In addition to the light-emitting layer, the organic layer may have 1) a hole transport layer/a light-emitting layer, 2) a light-emitting layer/an electron transport layer, 3) a hole transport layer/a light-emitting layer/an electron transport layer, 4) a hole injection layer/a hole transport layer/a light-emitting layer/an electron transport layer, or 5) a hole injection layer/a hole transport layer/a light-emitting layer/an electron transport layer/an electron injection layer that form a stacked structure. In addition, each of the layers may be a single layer or multiple layers. When the structures of 1) to 5) are used, the anode side electrode is connected to the hole injection layer or the hole transport layer, and the cathode side electrode is connected to the electron injection layer or the electron transport layer.

The hole transport layer may be formed by staking or mixing one or more hole transport materials, or by using mixture of a hole transport material and a high molecular adhesive. The hole transport material needs to efficiently transport holes from the anode between electrodes with electric field applied, so it is desired that the efficiency of hole injection is high, and the injected holes can be efficiently transported. For this reason, the hole transport material should have appropriate ionic potential and high hole mobility, therefore the material displays superior stability and prevents generation of impurities that may form traps during manufacturing and use. Any material satisfying such requirement may be used, including but not limited to benzidines, such as 4,4'-bis(N-(3-methylphenyl)-N-phenyl amino) biphenyl (TPD); 4,4'-bis(N-(1-naphthyl)-N-phenyl amino)biphenyl (NPD); 4,4'-bis(N,N-bis(4-biphenyl)amino) biphenyl (TBDB); bis(N,N-diphenyl-4-phenylamino)-N,N-diphenyl-4,4'-diamino -1,1'-biphenyl (TPD232); and material sets that are so-called star-shaped triarylamines, such as 4,4', 4"-tris(3-methylphenyl (phenyl)amino)triphenylamine (m-MTDATA), 4,4', 4"-tris(1-naphthyl (phenyl)amino)triphenylamine (1-TNATA), materials having carbazole-based structure, which are preferably carbazole-based compounds, including dicarbazole derivatives such as bis(N-aryl carbazole) and bis(N-alkyl carbazole), triscarbazole derivatives and tetracarbazole derivatives, heterocyclic compounds such as triphenyl compounds, pyrazoline derivatives, stilbene-containing compounds, hydrazine-containing compounds, benzofuran derivatives, thiophene derivatives, oxadiazole derivatives, phthalocyanine derivatives and porphyrin derivatives and fullerene derivatives. In polymers, more preferable are polycarbonates whose side chain has the foregoing monomers or styrene derivatives, polythiophene, polyaniline, polyfluorene, poly vinyl carbazole and polysilane. Also, inorganic compounds such as P-type Si and P-type SiC may be used.

A hole injection layer may be provided between the anode and the hole transport layer. Setting the hole injection layer helps to reduce driving voltage and improve durability life of the resultant organic light-emitting element. The hole injection layer is preferably made of a material whose ionic potential is lower than that of the hole transport layer. Particularly, the material may be a biphenyl amine derivative like TPD232, or a star-shaped triarylamine material set. A phthalocyanine derivative may be also used. In addition, it is preferable that the hole injection layer is made of a receptor compound alone, or the receptor compound is used by being doped into other hole transport layers. The receptor compounds may be, for example, metallic chlorides such as ferric trichloride (III), aluminum chloride, gallium chloride, indium chloride, and antimony chloride; metallic oxides such as molybdenum oxide, vanadium oxide, tungsten oxide, and ruthenium oxide; and charge-transfer ligands such as tris(4-bromophenyl) aminium hexachloroantimonate (TBPAH). Also, the receptor compounds may be organic compounds whose molecules contain nitryl, cyano, halogen or trifluoromethyl; quinone-containing compounds; estolide-containing compounds; and fullerene.

In the present invention, the light-emitting layer may be a single layer or multiple layers, and may be individually made of light-emitting materials (a host material and a doping material). It may either be a mixture of the host material and the doping material, or it may be the host material itself, either case may work. In other words, in the light-emitting layer of the disclosed light-emitting element, it may be that only the host material emits light or only the doping material emits light, or the host material and the doping material emit light together. Considering from using the power efficiently and obtaining the light of high color purity, it is preferable that the light-emitting layer is made by mixing the host material and the doping material. Furthermore, the host material and the doping material may be a single material or a combination of multiple materials, either case may work. The doping material may be added into the whole host material, or may be added into part of the host material, either case may work. Doping materials may be stacked into layers, or may be dispersed, either case may work. The doping material may control the color of light emitted. Excess addition of the doping material may lead to concentration quenching. Therefore, the dosage of the doping material with respect to the host material is preferably 20 weight% or less, more preferably is 10 weight% or less. Doping methods may be achieved by evaporation together with the host material, or may be processed by evaporation after being mixed with the host material.

The light-emitting material, particularly, may use condensed nucleus derivatives conventionally known as light-emitting element, including anthracene and pyrene; metal-chelating hydroxyquinoline compounds, including tris(8-hydroxyquinoline)aluminum; dibenzofuran derivatives; carbazole derivatives; indolocarbazole derivatives; and polymers, including polyphenylene vinylidene derivatives, ploy(p-phenylene) derivatives, and polythiophene derivatives, without particular limitation.

The host material included in the light-emitting material is not limited herein, and may be compounds having condensed arylcyclic structure or derivatives thereof such as anthracene, phenanthrene, pyrene, benzophenanthrene, tetracene, perylene, benzo[9,10]phenanthrene, fluoranthene, fluorene, and indene; aromatic amine derivatives, such as N,N'-dinaphthyl-N,N'-diphenyl-4,4'-diphenyl-1,1'-diamine; metal-chelating hydroxyquinoline compounds such as tris (8-hydroxyquinoline)aluminum; pyrrolopyrrole derivatives, dibenzofuran derivatives; carbazole derivatives; indolocarbazole derivatives; and triazine derivatives. In these polymers, poly phenylene vinylidene derivatives, poly(p-phenylene) derivatives, polyfluorene derivatives, polyvinyl carbazole derivatives, and polythiophene derivatives may be used without particular limitation.

In addition, the doping material is not limited herein, and may be compounds having condensed arylcyclic structure such as naphthalene, anthracene, phenanthrene, pyrene, benzophenanthrene, perylene, benzo[9,10]phenanthrene, fluoranthene, fluorene, and indene, or derivatives thereof (e.g. 2-(benzothiazole-2-yl)-9,10-diphenyl anthracene); and compounds having heteroaromatic rings such as furan, pyrrole, thiophene, silole, 9-silicon heterofluorene, 9,9'-spiro two silicon heterofluorene, benzothiophene, benzofuran, indole, dibenzothiophene, dibenzofuran, imidazolopyridine, phenanthroline, pyridine, pyrazine, naphthyridine, quinoxaline, pyrrolopyridine, and thioxanthene or derivatives thereof; borane derivatives, distyryl benzene derivatives, aminostyryl derivatives, pyrromethene derivatives, diketone pyrrolo[3,4-c]pyrrole derivatives, coumarin derivatives, zole derivatives such as imidazole, thiazol, thiadiazole, carbazole, oxazole, oxadiazole, and triazole; and aromatic amine derivatives.

Moreover, the light-emitting layer may dope a phosphorescent material therein. The phosphorescent material is a material that phosphoresces at room temperature. When a phosphorescent material is used as a doping agent, there is no particular limitation as long as it phosphoresces at room temperature. The material is preferably an organic metallic complex containing at least one selected from indium, ruthenium, rhodium, palladium, platinum, osmium and rhenium. Considering from achieving high efficiency of phosphorescence at room temperature, it contains more preferably an organic metallic clathrate of indium or platinum. The host material used with such phosphorescent doping agent, below compounds may be well used. The compounds and derivatives include indole derivatives, carbazole derivatives, indolocarbazole derivatives, nitrogen-containing aromatic compound derivatives containing pyridine-, pyrimidine- or triazine-structure, aromatic compound derivatives such as polyaryl benzene derivatives, spirofluorene derivatives, truxene, benzo[9,10]phenanthrene, compounds containing chalcogens such as dibenzofuran derivatives and dibenzothiophene, and organic metallic clathrates such as hydroxyquinolineberyllium clathrate. Basically, there is no additional limitation, as long as the triplet energy level of these materials is higher than that of the selected doping agent, electrons and holes can be successfully injected or transported from the layers where they are in. Besides, the light-emitting layer may contain two or more triplet-state light-emitting doping agents, and/or two or more host materials. Moreover, the light-emitting layer may contain one or more triplet-state light-emitting doping agents and one or more fluorescence doping agents.

In the present invention, the electron transport layer is a layer where electrons are injected from the cathode and then transported. The electron transport layer preferably has high efficiency of electron injection and may transport the injected electrons efficiently. Therefore, the electron transport layer is preferably made of a material that has high electron affinity, high electron mobility, and superior stability, and is unlikely to generate impurities that may form traps during manufacturing and use. However, in the consideration of transport balance of holes and electrons, if the electron transport layer is mainly used to effectively prevent the holes from the anode from getting combined and flowing to the cathode side. Even if the electron transport layer is made of a material which the electron transport capability is not so high, the effect of improving light-emitting efficiency is the same as that where a material having high electron transporting ability is used. Hence, in the electron transport layer of the present invention, a hole blocking layer that prevents holes from hole migration is also included as an equivalent.

The electron transport material used in the electron transport layer is not limited herein, and may be condensed arylcyclic derivatives such as naphthalene and anthracene; styryl-based aromatic cyclic derivatives such as 4,4'-bis (diphenyl vinyl)biphenyl; quinone derivatives such as anthraquinone and biphenyl quinone; phosphine oxide derivatives; hydroxyquinoline clathrates such as tris(8-hydroxyquinoline)aluminum; benzohydroxy quinoline clathrates, hydroxyzole clathrates, azomethine clathrates, tropolone metallic clathrates or flavonol metallic clathrates. For reducing the driving voltage and obtaining a high efficient light-emitting, it is preferably a compound having heteroaromatic-ring structure. The heteroaromatic-ring structure is composed of elements selected from carbon, hydrogen, nitrogen, oxygen, silicon, and phosphorous, and containing electron-withdrawing nitrogen.

Electron-withdrawing nitrogen containing heteroaromatic rings have high electron affinity. An electron transport material containing electron-withdrawing nitrogen tends to receive electrons coming from the cathode having high electron affinity, thereby reducing the driving voltage required by the light-emitting element. In addition, since supply of electrons to the light-emitting layer increases, the probability of recombination in the light-emitting layer is increased, therefore the light-emitting efficiency is improved. Heteroaromatic rings containing electron-withdrawing nitrogen include, for example, pyridine ring, pyrazin ring, pyrimidine ring, quinoline ring, quinoxaline ring, naphthyridine ring, pyrimidopyrimidine ring, benzoquinoline ring, phenanthroline ring, imidazole ring, oxazole ring, oxadiazole ring, triazole ring, thiazole ring, thiadiazole ring, benzooxazole ring, benzothiazole ring, benzoimidazole ring, and phenanthroimidazole ring.

Besides, compounds having theses heteroaromatic rings include, for example, low polypyridine derivatives such as benzoimidazole derivatives, benzooxazole derivatives, benzothiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, bipyridine, terpyridine. When the derivative has condensed arylcyclic structure, glass transition temperature is raised and electron mobility increases. Thereby, the driving voltage of the light-emitting element can be significantly reduced, so it is preferred. In addition, in view of improving the durability life, fabrication easiness and material availability of the resultant light-emitting element, it is preferable that the foregoing condensed arylcyclic structure is anthracene-based structure, pyrene-based structure or phenanthroline-based structure.

The aforementioned electron transport materials may be used alone, or may be used in a combination of two or more thereof, or may be used having one or more other electron transport materials mixed thereto. In addition, a donor compound may be added thereto. Herein, the donor compound refers to a compound that the electric conductivity of the electron transport layer is improved by improving electron-injection energy barrier and making electrons easily enter the electron transport layer from the cathode or the electron injection layer. In the present invention, such a donor compound is preferably, for example, an alkaline metal, an inorganic salt containing alkaline metal, a clathrate of an alkaline metal and an organic substance, an alkaline earth metal, an inorganic salt containing alkaline earth metal and a clathrate of an alkaline earth metal and an organic substance. Preferable alkaline metal or alkaline earth metal may be alkaline metal having low work function and effectively improved electron transport capability, such as lithium and sodium and cesium and alkaline earth metals such as magnesium and calcium. In the present invention, an electron injection layer may be provided between the cathode and the electron transport layer. Typically, the electron injection layer is inserted for moving electrons from the cathode to the electron transport layer. When it is inserted, the electron injection layer may be made of a compound of heteroaromatic-ring structure containing electron-withdrawing nitrogen, and may be a layer containing the foregoing donor compounds. Moreover, in the electron injection layer, inorganic substances such as insulators or semiconductors may be used.

Use of these materials effectively prevents the light-emitting element from short circuit, and improves electron injection, thus these materials are preferred. The insulator may be at least one metallic compound selected from alkaline metal chalcogenides, alkaline earth metal chalcogenides, alkaline metal halides and alkaline earth metal halides. In addition, clathrates of organic substances and metals may be used well.

The method for making the layers of the light-emitting element as described above, may be resistance heating evaporation, electron-beam evaporation, sputtering, molecular stacking, or coating, without particular limitation. However, for better properties of the resultant element, resistance heating evaporation or electron-beam evaporation is more preferable. The thickness of the organic layer depends on the resistance of the light-emitting substance and it is not limited herein, thickness of 1 to 1000 nm may be preferable. Each of the light-emitting layer, the electron transport layer, and the hole transport layer has film thickness of preferably 1 nm or more and 200 nm or less, more preferably 5 nm or more and 100 nm or less.

The light extraction efficiency improving layer used in the present invention contains a compound of a thiophene-based structure, a furan-based structure or a pyrrole-based structure described above For maximizing light-emitting efficiency and realizing the color reproducibility, it is preferable that compounds of the thiophene-based structure, the furan-based structure or the pyrrole-based structure are stacked in a thickness of 20 nm to 120 nm, more preferably in a thickness of 40 nm to 80 nm. Also for maximizing light-emitting efficiency, it is even more preferably the layer for improving light extraction efficiency has thickness of 50nm to 70nm.

The method for forming the light extraction efficiency improving layer is not limited, may be resistance heating evaporation, electron-beam evaporation, sputtering, molecular stacking, coating, ink-jet, dragging, or laser transfer.

The disclosed light-emitting element converts electricity into light. Herein, the electricity may use direct current or pulse current or alternating current. The current and voltage used are not limited, for better power consumption and service life of the resultant element, selection shall be made to achieve maximum illumination with minimum energy.

The disclosed light-emitting element is very suitable for flat-panel displays that display information in the form of a matrix and/or as columns.

In matrix-based displays, congregation of pixels for presenting texts or images are arranged in two-dimensional configuration, such as a grid or a mosaic. The pixel has a shape and a size depending on its applications. For example, for presenting texts and images in computers, monitors, and TV sets, quadrilateral pixels are used, and each of the pixels has a side-length of 300 um or less. In addition, for large-sized displays such as billboards, pixels used may have a side-length of the mm scale. For monochromatic display, all the arranged pixels are of the same colors. For chromatic display, red, green, and blue pixels are arranged in a certain pattern. In this case, a triangular pattern or a stripe pattern is typically used. Moreover, the matrix may be driven by a line-by-line method or using an active matrix. While a line-by-line method is structurally simple, its operational properties in some cases may be inferior to those of an active matrix. Thus, it is important to use the two approaches flexibly according to the practical use.

As mentioned in the present invention, column-based display involves arranging pixels into a pattern and making areas defined by the pattern emit light, to show the predetermined information. Such applications may include time and temperature indications in digital clocks and thermometers, working state indications for audio systems and electromagnetic stoves, and indications of in-car information modules. The aforementioned matrix display and column display may be incorporated in a single panel.

The disclosed light-emitting element is a preferrable light source for illumination, as it is thinner and lighter than the existing device, and capable of planar light-emitting.

EXAMPLES

The aromatic amine compound disclosed in the present invention will be described with reference to the following examples. However, the present invention is not limited to the aromatic amine compound and the synthesis methods recited in the examples.

Dimethylformamide, ethyl acetate, 1,2-dimethylbenzene, potassium carbonate, dichloromethane, ethanol and ethanol-sodium carbonate were purchased from China National Medicines Corporation Ltd. N-methylpyrrole and 2,5-dibromothiophene were purchased from TCI Co. Various palladium catalysts, boronic acid derivatives and boronic acid ester derivatives were purchased from Aldrich Co.

$^1$H-NMR spectrums were obtained using a nuclear magnetic resonance spectrometer (JEOL; 400 MHz) and HPLC chromatograms were obtained using a high-performance liquid chromatography (Shimadzu; LC-20AD).

In the described Examples and Comparative Examples, the following compounds were used:
Compound [2] (2,5-bis(4-(N-phenyl)-(N-3-pyridyl) aminophenyl)thiophene),
Compound [5] (2,5-bis(4-(N-4-biphenyl)-(N-3-pyridyl) aminophenyl)thiophene),
Compound [6] (2,5-bis(4-(N-4-biphenyl)-(N-4-pyridyl) aminophenyl)thiophene),
Compound [8] (2,5-bis(4-(N-3-biphenyl)-(N-3-pyridyl) aminophenyl)thiophene),
Compound [87] (1-methyl-2,5-bis(4-(N-4-biphenyl)-(N-3-pyridyl) aminophenyl)-1H-pyrrole),
Compound [31] (2,5-bis(4-(N-1-naphthyl)-(N-4-pyridineamino)phenyl)thiophene),
Compound [32] (2,5-bis(4-(N-3-biphenyl)-(N-4-pyridineamino)phenyl)thiophene),
Compound [134] (2,5-bis(4-(N-3-(3'-methyl)biphenyl)-(N-4-pyridineamino) phenyl)thiophene),
Compound [11] (2,5-bis(4-(N-4-(3-pyridinyl)phenyl)-(N-3-pyridineamino) phenyl)thiophene),
Compound [12] (2,5-bis(4-(N-4-(3-pyridinyl)phenyl)-(N-4-pyridineamino) phenyl)thiophene),
Compound [13] (2,5-bis(4-(N-4-(4-pyridinyl)phenyl)-(N-2-pyridineamino) phenyl)thiophene),
Compound [14] (2,5-bis(4-(N-4-(4-pyridinyl)phenyl)-(N-3-pyridineamino) phenyl)thiophene),
Compound [15] (2,5-bis(4-(N-4-(4-pyridinyl)phenyl)-(N-4-pyridineamino) phenyl)thiophene),
Compound [18] (2,5-bis(4-(N-3-(3-pyridinyl)phenyl)-(N-4-pyridineamino) phenyl)thiophene),
Compound [21] (2,5-bis(4-(N-3-(4-pyridinyl)phenyl)-(N-4-pyridineamino) phenyl)thiophene),
Compound [140] (2,5-bis(4-(N-4-biphenyl)-(N-3-quinolineamino) phenyl)thiophene),
Compound [142] (2,5-bis(4-(N-4-biphenyl)-(N-6-quinolineamino) phenyl)thiophene),
Compound [143] (2,5-bis(4-(N-4-biphenyl)-(N-2-pyrimidineamino) phenyl)thiophene),
Compound [144] (2,5-bis(4-(N-4-biphenyl)-(N-5-pyrimidineamino) phenyl)thiophene),
Compound [147] (2,5-bis(4-(N-4-biphenyl)-(N-4-phenylamino) phenyl)thiophene),
Compound [148] (2,5-bis(4-(N-4-biphenyl)-(N-1-naphthalyne amino) phenyl)thiophene),
Compound [149] (2,5-bis(4-(N-4-(biphenyl)-(N-2-naphthalyne amino) phenyl)thiophene),
NPD: (N,N'-diphenyl -N,N'-bis(1-naphthyl)-1,1'-biphenyl -4,4'-diamine),
F4-TCNQ (2,3,5,6-tetrafluoro-7,7',8,8'-tetracyanodimethyl p-benzoquinone),
BH: (9-(2-naphthyl)-10-(4-(1-naphthyl)phenyl)anthracene),
BD: (E-7-(4-(diphenyl amino)styryl)-N,N-diphenyl -9,9'-dimethylfluorenyl-2-amine),
Alq$_3$: (tris(8-hydroxyquinoline)aluminum),
TBDB: (N,N,N',N'-4(4-biphenyl) biphenyl diamine).

For each compound described herein, in case the chemical denomination and the structural formula of the compound are both given herein, the structure of the compound is subject to the structural formula.

Example 1

Synthesis of Compound [2]

Under nitrogen atmosphere, 24.2 g of 2,5-dibromothiophene (100 mmol), 34.4 g of 4-chlorophenylboronic acid (220 mmol), 5.7 g of tetra-(triphenylphosphine)palladium (5.0 mmol), 200 ml of water solution of 1.5M sodium carbonate (300 mmol) and 100 ml of dimethyl ether (DME) were added into a reactor, and stirred at 110° C. for one night. Then the mixture was cooled to the room temperature and filtered. The filtrate was separated into an organic layer and an aqueous layer. The organic layer was condensed under reduced pressure. The collected solid was washed with ethanol, and 21.3 g of 2,5-bis(4-chlorophenyl)thiophene was obtained.

$^1$HNMR(DMSO): δ7.52~7.51(d, 8H), 6.32(s,2H), 3.57(s, 3H).

Under nitrogen atmosphere, 2.00 g of 2,5-bis(4-chlorophenyl)thiophene (6.56 mmol), 2.45 g of N-phenyl -3-pyridyl amine (14.4 mmol), 189 mg of bis(dibenzylideneacetone)palladium (0.328 mmol), 190 mg of tri-tert-butylphosphine tetrafluoroborate (0.656 mmol), 1.89 g of sodium tert-butoxide (19.7 mmol) and 60 ml of 1,2-dimethylbenzene were added into an reactor, and stirred at 110° C. for one night. Then the mixture was cooled to the room temperature and filtered. The filtrate was condensed under reduced pressure. The collected solid was washed with ethanol, and 3.5 g of crude product was obtained. The crude product was sublimated under 3×10$^{-3}$ Pa, 280° C., and 2.2 g of Compound [2] (pale yellow solid) was obtained.

$^1$HNMR(CDCl$_3$): δ7.53~7.51(d,4H), 7.42~7.39(m,2H), 7.32~7.28(t,4H), 7.20(s,2H), 7.19~7.15(m,2H), 7.14~7.07 (m,10H).

HPLC (purity=97.1%)

Example 2

Synthesis of Compound [5]

All the other conditions were the same as those in Example 1, except that N-(4-biphenyl)-3-pyridyl amine was used instead of N-phenyl-3-pyridyl amine, and 1.1 g of Compound [5] (pale yellow solid) was obtained.

$^1$HNMR(DMSO): δ8.47~8.46(d,2H), 8.27~8.26(d,2H), 7.57~7.52(m,12H), 7.45~7.41(m,6H), 7.35~7.32(t,2H), 7.25~7.12(m,12H).

HPLC (purity=98.1%)

Example 3

Synthesis of Compound [6]

All the other conditions were the same as those in Example 1, except that N-(4-biphenyl)-3-pyridyl amine was used instead of N-phenyl-4-pyridyl amine, and 2.2 g of Compound [6] (pale yellow solid) was obtained.

$^1$HNMR(DMSO): δ8.26~8.25(d,4H), 7.76~7.67(m,12H), 7.55(s,2H), 7.48~7.45(t,4H), 7.38~7.26(m, 10H), 6.78~6.77 (m, 4H).

HPLC (purity=99.02%)

Example 4

Synthesis of Compound [8]

All the other conditions were the same as those in Example 1, except that N-(3-biphenyl)-3-pyridyl amine was used instead of N-phenyl-3-pyridyl amine, and 1.5 g of Compound [8] (pale yellow solid) was obtained.

$^1$HNMR(CDCl$_3$): δ8. 35~8.34(d,2H), 8.27~8.26(d,2H), 7. 66~7. 64(d,4H), 7.58~7. 56(d,4H), 7.53~7.41(m,12H), 7.37~7.34(m,6H), 7.12~7.08(t,6H). HPLC (purity=97.8%)

Example 5

Synthesis of Compound [31]

All the other conditions were the same as those in Example 1, except that N-(3-biphenyl)-3-pyridyl amine was used instead of N-naphthyl-3-pyridyl amine, and 2.5 g of Compound [31] (pale yellow solid) was obtained.

$^1$HNMR(CDCl3): δ8.17~8.14(d,4H), 8.05~7.98(m,4H), 7.82~7.79(d,2H), 7.67~7.59(m,6H), 7.57~7.43(m,8H), 7.30~7.27(d,4H), 6.56~6.54(d,4H).

HPLC (purity=97.2%)

Example 6

Synthesis of Compound [32]

All the other conditions were the same as those in Example 1, expect that N-(3-biphenyl)-3-pyridyl amine was used instead of N-biphenyl-3-pyridyl amine, and 3.2 g of Compound [32] (pale yellow solid) was obtained.

$^1$HNMR (CDCl3): δ8.17~8.14(d,4H), 8.05~7.98(m,4H), 7.82~7.79(d,2H), 7.67~7.59(m,6H), 7.57~7.43(m,8H), 7.30~7.27(d,4H), 6.56~6.54(d,4H).

HPLC (purity=95.0%)

Example 7

Synthesis of Compound [134]

All the other conditions were the same as those in Example 1, except that N-phenyl-3-pyridyl amine was used instead of N-3-(3'-methylbiphenyl)-4-pyridyl amine, and 3.6 g of Compound [134] (pale yellow solid) was obtained.

$^1$HNMR (CDCl3) δ8.25(d,4H); 7.70~7.75(m,8H); 7.54(s, 2H); 7.44~7.49(m,4H); 7.15~7.36(m,12H); 6.76(d,4H); 2.37(s,6H).

HPLC (purity=95.9%)

Example 8

Synthesis of Compound [87]

Under nitrogen atmosphere, 3.24 g of N-methylpyrrole (40 mmol), 22.9 g of 4-chlorobromobenzene (120 mmol), 243 mg of bis(diphenyl phosphine) propane-palladous chloride (0.39 mmol), 15.68 g of potassium carbonate (160 mmol) and 150 ml of dimethylacetamine (DMAC) were added into an reactor, and stirred at 110° C. for one night. Then the mixture was cooled to the room temperature and filtered. The filtrate was condensed under reduced pressure. The collected solid was washed with ethanol, and 4.3 g of 2,5-bis(4-chlorophenyl)-1-methylpyrrole was obtained.

$^1$HNMR(DMSO): δ7.52~7.51(d,8H), 6.32(s,2H), 3.57(s, 3H).

Under nitrogen atmosphere, 1.50 g of 2,5-bis(4-chlorophenyl)-1-methylpyrrole (4.96 mmol), 3.50 g of N-(4-biphenyl)-3-pyridyl amine (14.2 mmol), 30 mg of bis(dibenzylideneacetone) palladium (0.052 mmol), 30 mg of tri-tert-butylphosphine tetrafluoroborate (0.10 mmol), 2.80 g of sodium tert-butoxide (29.1 mmol) and 60 ml of 1,2-dimethylbenzene were added into an reactor, and stirred at 110° C. for one night. Then the mixture was cooled to the room temperature and filtered. The filtrate was condensed under reduced pressure. The collected solid was washed with ethanol, and purified on a silica gel column (eluant: dichloromethane/ethyl acetate=4/1), and 2.4 g of crude product was obtained. The crude product was sublimated under $2\times10^{-3}$ Pa, 320° C., 1.0 g of Compound [87] (pale yellow solid) was obtained.

$^1$HNMR (CDCl$_3$): δ8.48~8.47(d,2H), 8.27~8.26(dd,2H), 7.59~7.57(d,4H), 7.55~7.53(d,4H), 7.50~7.47(m,2H), 7.45~7.38(m,8H), 7.35~7.31(t, 2H), 7.22~7.16(m, 10H), 6.31(s,2H), 3.66(s,3H).

HPLC (purity=97.8%)

Example 9

Preparation of Thin-Film Samples

An alkali-free glass substrate (Asahi Glass Co., Ltd., AN100) was washed by UV ozone for 20 minutes and placed into a vacuum evaporator. Air exhaust was performed until the degree of vacuum in the evaporator became higher than $1\times10^{-3}$ Pa. Under this condition, thin film of 50 nm of Compound [2] was deposited on the substrate through resistance heating evaporation. The speed for evaporation was 0.1 nm/s.

The refractive index and attenuation coefficient of the thin-film sample prepared above were measured in Toray Research Center Inc. by using an ellipsometer (J.A.Woollam Co, Inc., M-2000).

TABLE 1

| Compound | Refractive Index (n) | | |
|---|---|---|---|
| | λ = 430 nm | λ = 460 nm | λ = 500 nm |
| [2] | 2.34 | 2.14 | 1.98 |

* Optical constants (refractive index: n, attenuation coefficient: k) were rounded off to second decimal place.

Examples 10 to 24 and Comparative Example 1

Example 10

All the other conditions were the same as those in Example 9, except that Compound [2] was replaced with Compound [5].

The organic light-emitting element was evaluated. The results are shown in Table 2.

Example 11

All the other conditions were the same as those in Example 9, except that Compound [2] was replaced with Compound [6].

The organic light-emitting element was evaluated. The results are shown in Table 2.

Example 12

All the other conditions were the same as those in Example 9, except that Compound [2] was replaced with Compound [8].

The organic light-emitting element was evaluated. The results are shown in Table 2.

Example 13

All the other conditions were the same as those in Example 9, except that Compound [2] was replaced with Compound [87].

The organic light-emitting element was evaluated. The results are shown in Table 2.

Example 14

All the other conditions were the same as those in Example 9, except that Compound [2] was replaced with Compound [11].

The organic light-emitting element was evaluated. The results are shown in Table 2.

Example 15

All the other conditions were the same as those in Example 9, except that Compound [2] was replaced with Compound [12].

The organic light-emitting element was evaluated. The results are shown in Table 2.

Example 16

All the other conditions were the same as those in Example 9, except that Compound [2] was replaced with Compound [13].

The organic light-emitting element was evaluated. The results are shown in Table 2.

Example 17

All the other conditions were the same as those in Example 9, except that Compound [2] was replaced with Compound [14].

The organic light-emitting element was evaluated. The results are shown in Table 2.

Example 18

All the other conditions were the same as those in Example 9, except that Compound [2] was replaced with Compound [15].

The organic light-emitting element was evaluated. The results are shown in Table 2.

Example 19

All the other conditions were the same as those in Example 9, except that Compound [2] was replaced with Compound [18].

The organic light-emitting element was evaluated. The results are shown in Table 2.

Example 20

All the other conditions were the same as those in Example 9, except that Compound [2] was replaced with Compound [21].

The organic light-emitting element was evaluated. The results are shown in Table 2.

Example 21

All the other conditions were the same as those in Example 9, except that Compound [2] was replaced with Compound [140].

The organic light-emitting element was evaluated. The results are shown in Table 2.

Example 22

All the other conditions were the same as those in Example 9, except that Compound [2] was replaced with Compound [142].

The organic light-emitting element was evaluated. The results are shown in Table 2.

Example 23

All the other conditions were the same as those in Example 9, except that Compound [2] was replaced with Compound [143].

The organic light-emitting element was evaluated. The results are shown in Table 2.

Example 24

All the other conditions were the same as those in Example 9, except that Compound [2] was replaced with Compound [144].

The organic light-emitting element was evaluated. The results are shown in Table 2.

Comparative Example 1

All the other conditions were the same as those in Example 9, except that Compound [2] was replaced with NPD.

The organic light-emitting element was evaluated. The results are shown in Table 2.

Experiments were conducted for Examples 10 to 24 same as in Example 9, and the results are shown in Table 2 below.

TABLE 2
| | Compound | Refractive Index (n) | | |
|---|---|---|---|---|
| | | λ = 430 nm | λ = 460 nm | λ = 500 nm |
| Example 10 | [5] | 2.45 | 2.29 | 2.10 |
| Example 11 | [6] | 2.48 | 2.25 | 2.12 |
| Example 12 | [8] | 2.37 | 2.17 | 2.01 |
| Example 13 | [87] | 2.01 | 1.93 | 1.87 |
| Example 14 | [11] | 2.32 | 2.20 | 2.01 |
| Example 15 | [12] | 2.31 | 2.15 | 2.00 |
| Example 16 | [13] | 2.21 | 2.07 | 1.90 |
| Example 17 | [14] | 2.46 | 2.29 | 2.08 |
| Example 18 | [15] | 2.33 | 2.19 | 2.03 |
| Example 19 | [18] | 2.27 | 2.11 | 1.95 |
| Example 20 | [21] | 2.40 | 2.24 | 2.11 |
| Example 21 | [140] | 2.33 | 2.11 | 1.96 |
| Example 22 | [142] | 2.36 | 2.20 | 2.06 |
| Example 23 | [143] | 2.36 | 2.13 | 1.98 |
| Example 24 | [144] | 2.33 | 2.19 | 2.00 |
| Comparative Example 1 | NPD | 1.99 | 1.92 | 1.87 |
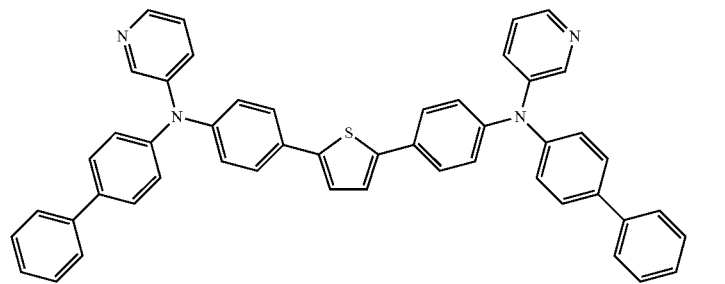
[5]
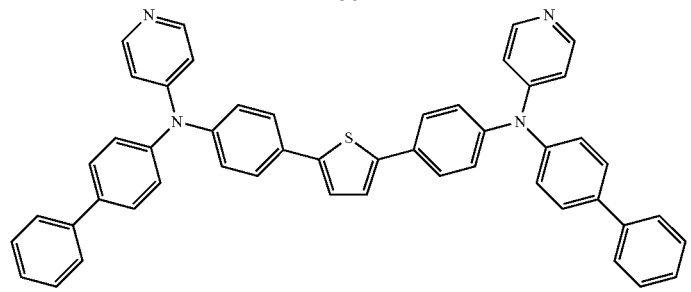
[6]
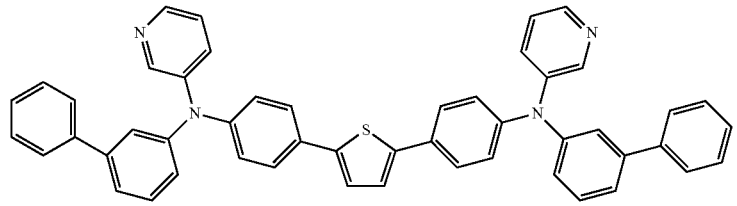
[8]
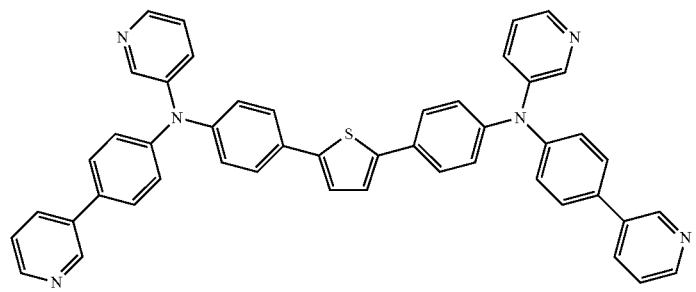
[11]

TABLE 2-continued

| | Refractive Index (n) | | |
|---|---|---|---|
| Compound | λ = 430 nm | λ = 460 nm | λ = 500 nm |

[12]

[13]

[14]

[15]

[18]

TABLE 2-continued

| | Refractive Index (n) | | |
|---|---|---|---|
| Compound | λ = 430 nm | λ = 460 nm | λ = 500 nm |

[21]

[87]

[140]

[142]

TABLE 2-continued
| | Refractive Index (n) | | |
|---|---|---|---|
| Compound | λ = 430 nm | λ = 460 nm | λ = 500 nm |
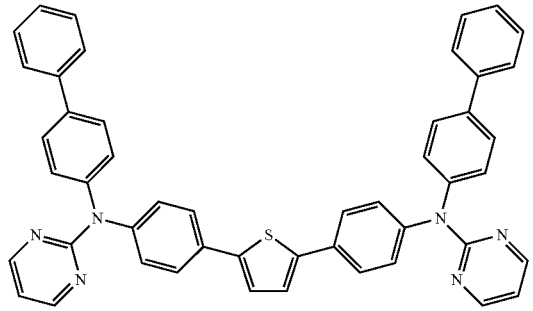
[143]
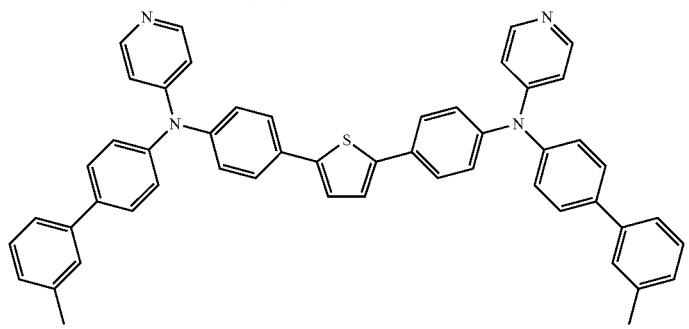 [SMILES: c1cc(-c2ccc(N(c3ccncc3)c3ccc(-c4ccc(-c5ccc(N(c6ccncc6)c6ccc(-c7ccncc7)cc6)cc5)s4)cc3)cc2)ccn1]
[134]
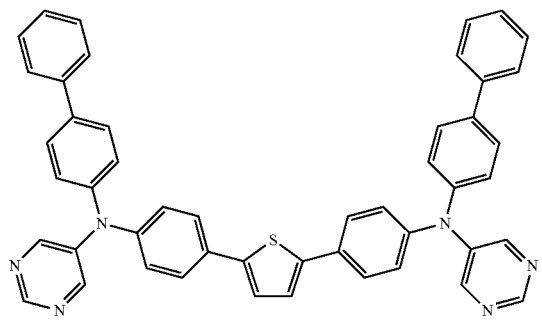
[144]
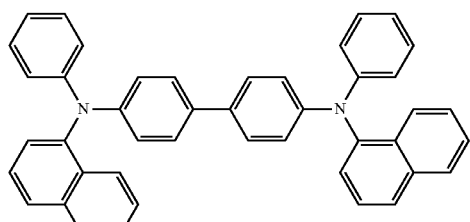
(NPD)

As shown in Table 1 and Table 2, Examples 9 to 24 exhibited higher refractive index compared with Comparative Example 1. The light-emitting elements were further tested for their performance.

Evaluation of Light-Emitting Elements

Example 25

Alkali-free glass was ultrasonically washed in isopropanol for 15 minutes, and washed by UV ozone for 30 minutes in the atmosphere. Vacuum evaporation was performed. The anode was first made by depositing 100 nm aluminum through evaporation. Then on the anode, a hole injection layer (NPD and F4-TCNQ (with a weight ratio of 97:3), 50 nm), a hole transport layer (NPD, 80 nm), a blue light-emitting layer (BH and BD (with a weight ratio of 97:3, 20 nm), an electron transport layer (Alq$_3$, 30 nm), an electron injection layer (LiF, 1 nm) were stacked in order through evaporation. Afterward, a translucent cathode was made of Mg and Ag (with a weight ratio of 10:1, 15 nm) through co-evaporation.

The compounds used are shown below.

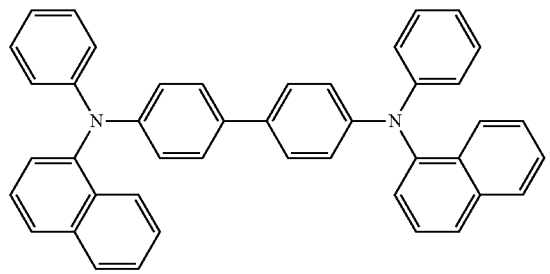

NPD

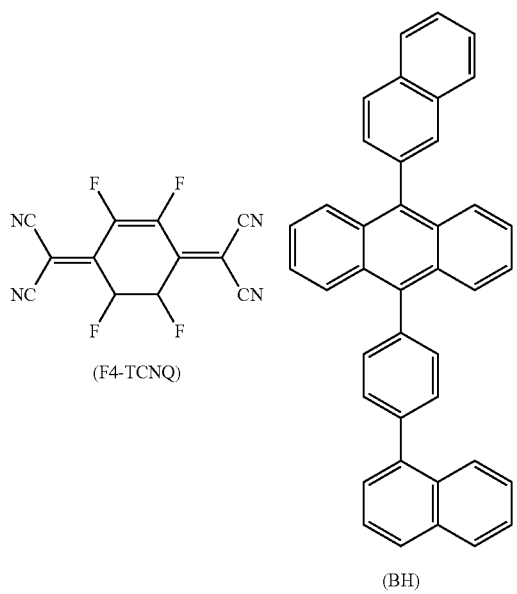

(F4-TCNQ)

(BH)

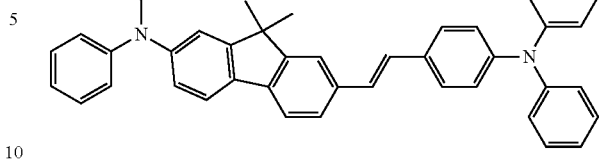

(BD)

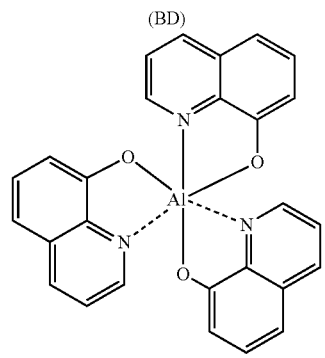

Alq$_3$

Then Compound [5] (60 nm) was deposited through evaporation to form a covering layer. Finally, under dry nitrogen atmosphere in a glove box, a sealing plate made of alkali-free glass was adhered to the light-emitting element using an epoxy binder.

At room temperature and at ambient atmosphere, direct current was applied to the light-emitting element at 10 mA/cm$^2$. A spectroradiometer (CS1000, Konica Minolta, Inc.) was used to test light emitting from the sealing plate in terms of illumination and color purity. The measurements were luminosity rate of 6.5 cd/A and color purity of CIE (x, y)=(0.139, 0.051). It was proven that the covering layer made of Compound [5] contributes to a high performance light-emitting element having high light-emitting efficiency and high color purity.

The results of evaluation are shown in Table 3.

Example 26

All the other conditions were the same as those in Example 25, except that the covering layer material was Compound [6]. The results of evaluation are shown in Table 3.

Example 27

All the other conditions were the same as those in Example 25, except that the covering layer material was Compound [8]. The results of evaluation are shown in Table 3.

Comparative Example 2

All the other conditions were the same as those in Example 25, except that the covering layer material was NPD. The results of evaluation are shown in Table 3.

Comparative Example 3

All the other conditions were the same as those in Example 25, except that the covering layer material was TBDB. The results of evaluation are shown in Table 3.

In Examples 28 to 39 and Comparative Examples 4 to 6, all the other conditions were the same as those in Example 25, except that the compounds used are those shown in Table 3, and the elements similar to that of Example 25 were made for evaluation. The results of evaluation are shown in Table 3.

The compounds used in Comparative Example 4, Comparative Example 5, and Comparative Example 6 are shown below.

[147]

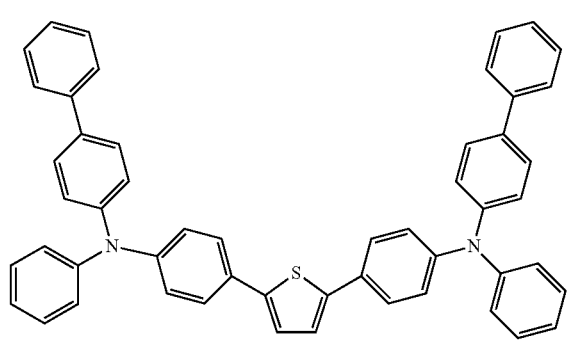

[148]

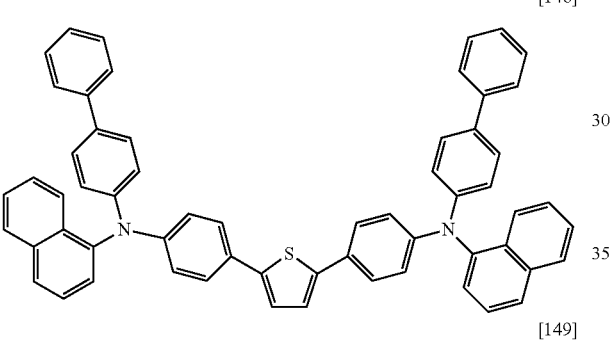

[149]

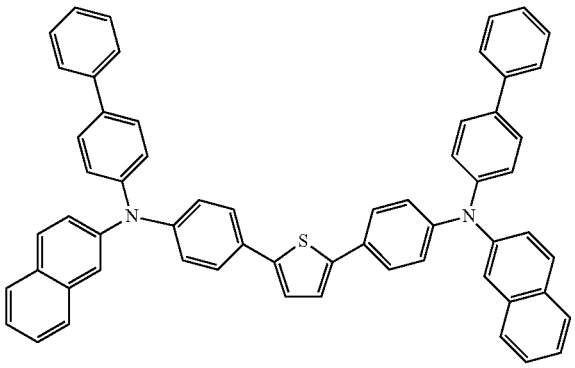

TABLE 3

| | Compound | Light-emitting efficiency (cd/A) | Color purity CIE (x, y) |
|---|---|---|---|
| Example 25 | [5] | 6.5 | 0.139, 0.051 |
| Example 26 | [6] | 6.8 | 0.139, 0.050 |
| Example 27 | [8] | 5.8 | 0.138, 0.049 |
| Example 28 | [2] | 6.6 | 0.139, 0.050 |
| Example 29 | [11] | 5.9 | 0.138, 0.052 |
| Example 30 | [12] | 6.2 | 0.138, 0.049 |
| Example 31 | [13] | 6.6 | 0.137, 0.049 |
| Example 32 | [14] | 6.8 | 0.139, 0.048 |

TABLE 3-continued

| | Compound | Light-emitting efficiency (cd/A) | Color purity CIE (x, y) |
|---|---|---|---|
| Example 33 | [15] | 6.1 | 0.139, 0.051 |
| Example 34 | [18] | 5.9 | 0.137, 0.051 |
| Example 35 | [21] | 6.0 | 0.139, 0.050 |
| Example 36 | [140] | 6.5 | 0.138, 0.049 |
| Example 37 | [142] | 6.5 | 0.139, 0.049 |
| Example 38 | [143] | 6.1 | 0.137, 0.050 |
| Example 39 | [144] | 6.1 | 0.137, 0.048 |
| Comparative Example 2 | NPD | 4.5 | 0.139, 0.048 |
| Comparative Example 3 | TBDB | 4.5 | 0.137, 0.051 |
| Comparative Example 4 | [147] | 4.6 | 0.137, 0.053 |
| Comparative Example 5 | [148] | 4.7 | 0.137, 0.050 |
| Comparative Example 6 | [149] | 4.4 | 0.138, 0.052 |

(TBDB)/Comparative Example 3

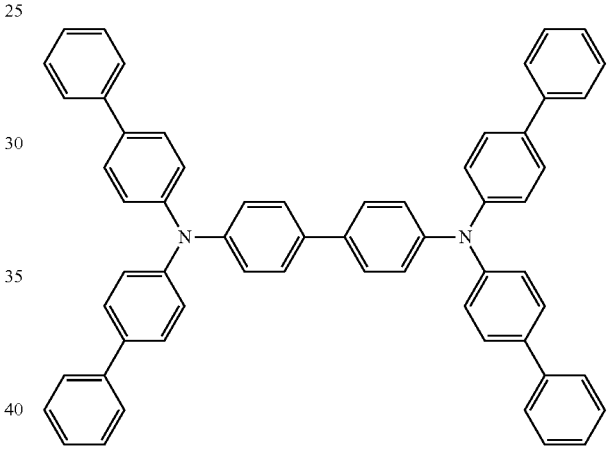

As shown in Table 3, the light-emitting elements of Example 25 to Example 39 provided both high light-emitting efficiency and high color purity. Additionally, the light-emitting elements of Comparative Example 2 to Comparative Example 6 had equivalent color purity compared with the light-emitting elements in the examples, however, their light-emitting efficiency was lower. This means they failed to provide high light-emitting efficiency and high color purity at the same time.

From the above results, the disclosed aromatic amine compound is suitable for the organic light-emitting element material, and may obtain light-emitting elements with both high light-emitting efficiency and high color purity. The aromatic amine compound is particularly suitable for the covering layer material.

All the patent documents and non-patent documents mentioned herein are incorporated into this application by reference. In the description, where "plural" is used it includes all cases which are greater than one. Also, where "one or more" is used it includes one, two, three and so on. For a range of number defined by having its upper and lower limits or a combination of its upper and lower limits stated herein, each of the upper and lower limits may be combined in any ways to form different ranges of number, and these combinations shall be formally deemed as effective as the range of number defined by the explicitly stated numbers. Without deviation from the gist of the present invention, people skilled in the art may perform modifications and variations of the present invention, these shall all be included in the scope of the present invention.

What is claimed is:

1. An organic light-emitting element, comprising in the following order:
   a substrate,
   a first electrode,
   one or more layers of an organic film comprising a light-emitting layer,
   a second electrode, and
   a covering layer comprising a compound represented by Formula (1):

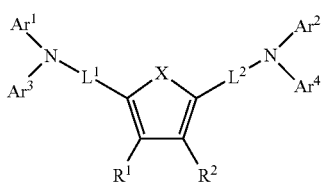

(1)

wherein
   X is a sulfur atom, an oxygen atom or N—R, wherein R is selected from hydrogen, deuterium, substitutable alkyl, substitutable cycloalkyl, substitutable heterocyclyl, substitutable alkenyl, substitutable cycloalkenyl, substitutable alkynyl, substitutable alkoxy, substitutable alkylthio, substitutable arylether, substitutable arylsulfide, substitutable aryl, substitutable heteroaryl, substitutable carbonyl, substitutable carboxyl, substitutable oxycarbonyl, substitutable carbamoyl, substitutable alkylamino and substitutable silyl;
   $L^1$, $L^2$ are identical or different, and each is independently selected from arylene or heteroarylene;
   $Ar^1$, $Ar^2$ are identical or different, and each is independently selected from aryl or heteroaryl;
   $Ar^3$, $Ar^4$ are identical or different, and each is independently selected from heteroaryl having at least one electron-withdrawing nitrogen atom which connects to an adjacent atom in the heteroaryl of $Ar^3$ or $Ar^4$ with a double bond; and
   $R^1$, $R^2$ are hydrogen.

2. The organic light-emitting element of claim 1, wherein $L^1$ and $L^2$ are arylene.

3. The organic light-emitting element of claim 1, wherein X is a sulfur atom.

4. The organic light-emitting element of claim 1, wherein the second electrode is a cathode and the covering layer is in direct contact with the cathode.

5. The organic light-emitting element of claim 1, wherein the compound represented by Formula (1) has a refractive index of greater than 2.07 (λ=460 nm).

* * * * *

UNITED STATES PATENT AND TRADEMARK OFFICE
CERTIFICATE OF CORRECTION

PATENT NO. : 10,700,308 B2
APPLICATION NO. : 15/108126
DATED : June 30, 2020
INVENTOR(S) : Jin et al.

Page 1 of 1

It is certified that error appears in the above-identified patent and that said Letters Patent is hereby corrected as shown below:

On the Title Page

Item [72], Lines 5-7, Inventors:

"Daisaku Tanaka, Otsu (JP)" should read --Daisaku Tanaka, Otsu-shi, Shiga (JP)--.

"Takeshi Ikeda, Otsu (JP)" should read --Takeshi Ikeda, Otsu-shi, Shiga (JP)--.

"Takuya Nishiyama, Otsu (JP)" should read --Takuya Nishiyama, Otsu-shi, Shiga (JP)--.

Signed and Sealed this
Eighteenth Day of August, 2020

Andrei Iancu
*Director of the United States Patent and Trademark Office*